United States Patent
Tsai et al.

(10) Patent No.: US 9,382,331 B2
(45) Date of Patent: Jul. 5, 2016

(54) ALPHA-ENOLASE SPECIFIC ANTIBODIES AND METHODS OF USES IN CANCER THERAPY

(71) Applicants: Development Center for Biotechnology, New Taipei (TW); National Health Research Institutes, Miaoli County (TW)

(72) Inventors: Shih-Chong Tsai, New Taipei (TW); Neng-Yao Shih, Tainan (TW); Ta-Tung Yuan, New Taipei (TW); Ko-Jiunn Liu, Tainan (TW); Shih-Chi Tseng, New Taipei (TW); Chih-Yung Hu, New Taipei (TW); Hsin-Yun Wang, New Taipei (TW); Li-Tzong Chen, Tainan (TW)

(73) Assignees: Development Center for Biotechnology, New Taipei (TW); National Health Research Institutes, Miaoli County (TW)

( * ) Notice: Subject to any disclaimer, the term of this patent is extended or adjusted under 35 U.S.C. 154(b) by 0 days.

(21) Appl. No.: 14/142,186

(22) Filed: Dec. 27, 2013

(65) Prior Publication Data
US 2015/0183884 A1    Jul. 2, 2015

(51) Int. Cl.
*A61K 39/395* (2006.01)
*C07K 16/40* (2006.01)
*G01N 33/574* (2006.01)
*A61K 39/00* (2006.01)

(52) U.S. Cl.
CPC .......... *C07K 16/40* (2013.01); *G01N 33/57492* (2013.01); *A61K 2039/505* (2013.01); *C07K 2317/34* (2013.01); *C07K 2317/55* (2013.01); *C07K 2317/73* (2013.01); *C07K 2317/76* (2013.01); *C07K 2317/92* (2013.01); *G01N 2333/988* (2013.01)

(58) Field of Classification Search
None
See application file for complete search history.

(56) References Cited

U.S. PATENT DOCUMENTS

| | | | |
|---|---|---|---|
| 6,348,580 B1 | 2/2002 | Fukui et al. | |
| 7,294,753 B2 | 11/2007 | Kloetzer et al. | |
| 7,408,041 B2 * | 8/2008 | Bowdish et al. | 530/387.3 |
| 7,452,678 B2 * | 11/2008 | Durham et al. | 435/7.1 |
| 7,473,531 B1 * | 1/2009 | Domon et al. | 435/7.1 |
| 2003/0018029 A1 | 1/2003 | Barker et al. | |
| 2013/0165458 A1 | 6/2013 | Huang et al. | |
| 2015/0175710 A1 * | 6/2015 | Tsai et al. | |

FOREIGN PATENT DOCUMENTS

| | | | |
|---|---|---|---|
| WO | 2008/089307 A2 | | 7/2008 |
| WO | 2011/041894 | * | 4/2011 |
| WO | 2012/138294 | * | 10/2012 |
| WO | 2012/175691 | * | 12/2012 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Campbell et al Monoclonal Antibody Technology published by Elseivers (1984) Chapter 1 pp. 1-32.*
PCT International Search Report and Written Opinion dated Sep. 26, 2014, issued in corresponding International Application No. PCT/US2013/076877 (17 pages).
NCBI, GenBank Accession No. AAB27638.1 (Sep. 30, 1993), "anti-bacterial ssDNA antibody heavy chain CDR2 region, partial [Mus sp.]". (1 page).
Leu, Sy-Jye, et al., "Generation and characterization of anti-a-enolase single-chain antibodies in chicken"; Veterinary Immunology and Immunopathology, vol. 137, No. 3, (2010) Elsevier B.V.; doi: 10.1016/j.vetimm.2010.06.001; pp. 251-260.
Hsiao, Kuan-Chung, et al., "Surface a-Enolase Promotes Extracellular Matrix Degradation and Tumor Metastasis and Represents a New Therapeutic Target"; PLOS One, vol. 8. No. 7, Article No. e69354; Jul. 2013; pp. 1-15.
Capello, Michela, et al., a-enolase: a promising therapeutic and diagnostic tumor target; FEBS Journal (2011, vol. 278, No. 7, pp. 1064-1074.
2nd Official Action dated Jan. 8, 2016, issued by the Taiwan Patent Office in related Taiwan Patent Application No. TW-102147152 (4 pages).

* cited by examiner

*Primary Examiner* — Sheela J Huff
(74) *Attorney, Agent, or Firm* — Osha Liang LLP

(57) ABSTRACT

The present invention discloses an anti-human alpha-enolase (ENO1) antibody, which can bind the peptides, comprising amino-acid sequence 296FD Q D D W G A W Q K F TA309 (SEQ ID: #9) and/or 326K R I A K A V N EK S336 (SEQ ID: #10) of human ENO1 protein (GenBank: AAH50642.1), has a favorable binding activity (the binding affinity is around 2.19×10-10 mol/L) and a remarkable capability to inhibit the cell invasion and tumor metastasis of a varied of tumors. The recognized peptides and antibody of the invention are useful for diagnosis, prognosis, and treatment of cancers that have been reported to express cell-surface ENO1 such as including lung, breast, pancreas, liver, colorectal, prostate cancers and solid tumors.

20 Claims, 30 Drawing Sheets

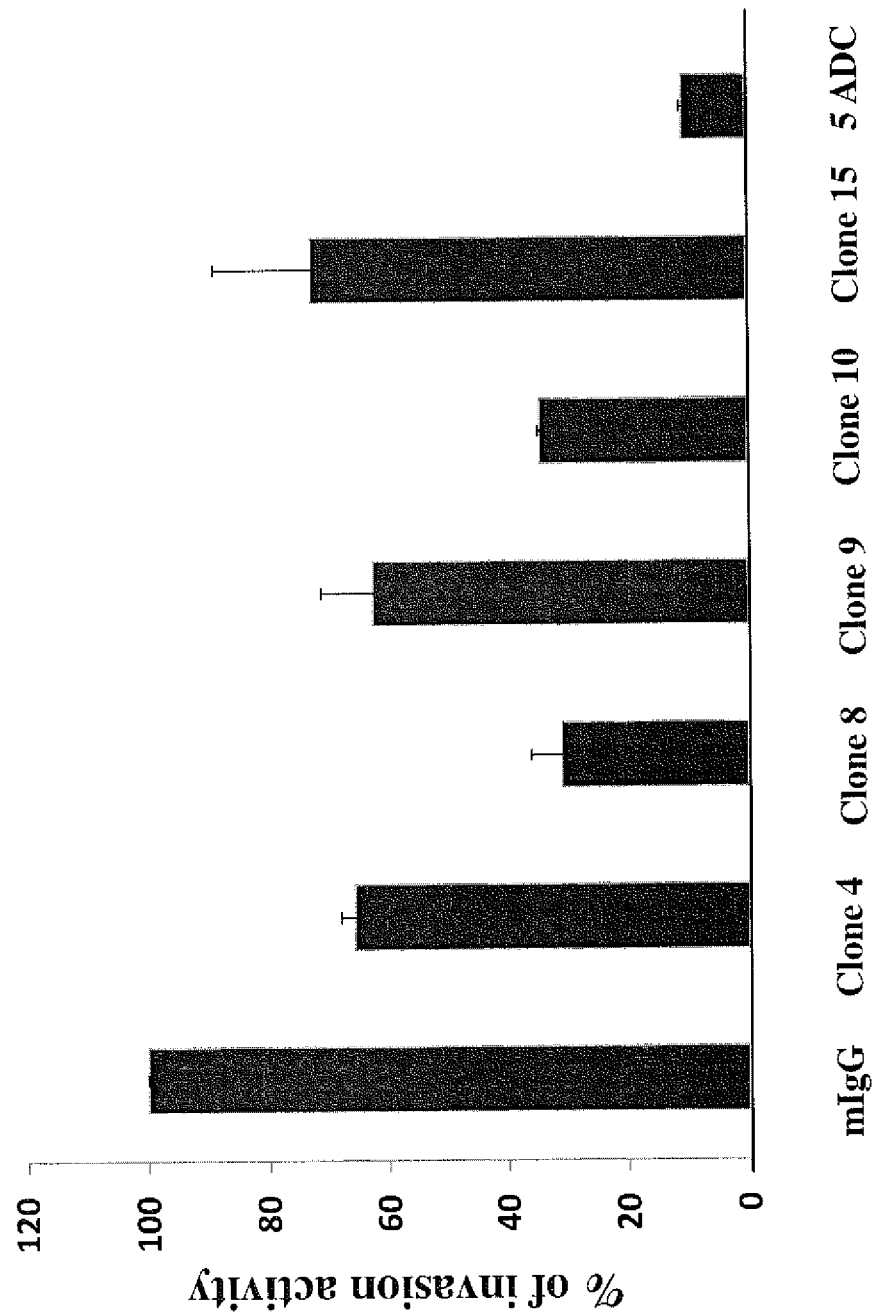

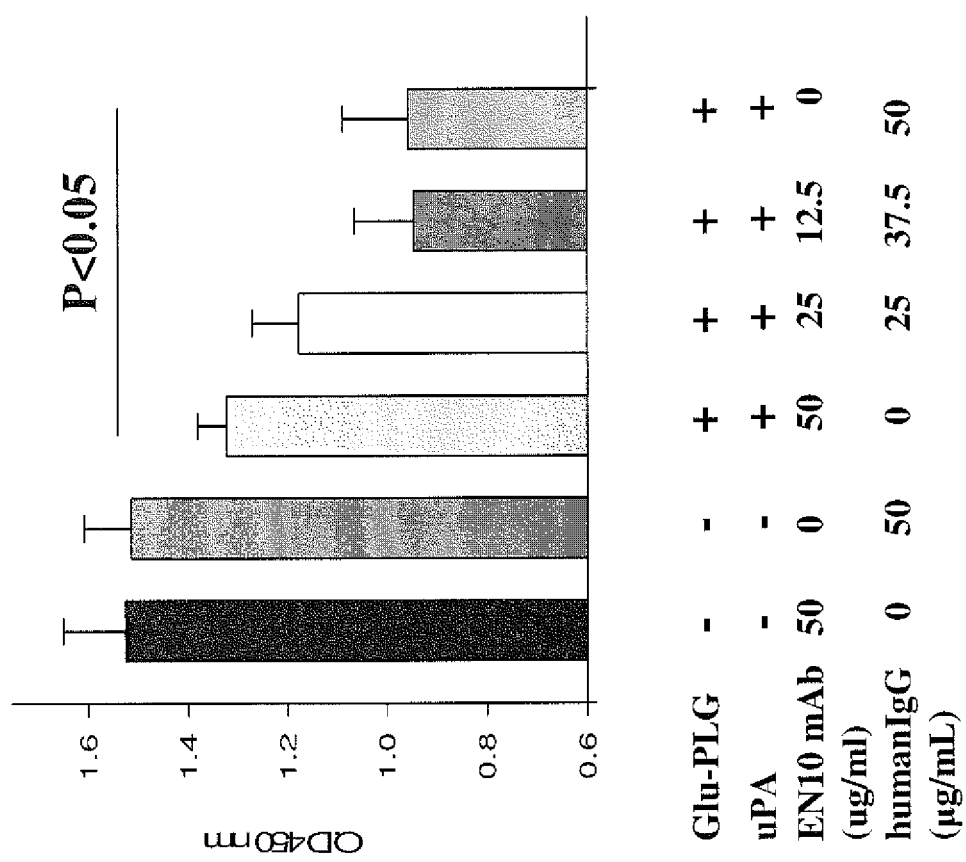

FIG. 11A

Kabat  1      5      10     15     20     25                      36     40
       EVQLQQSGPELVKPGASVKMSCKASGYTFTSCVMNWVKQKPGQG    SEQ ID NO:1
                    FR1                    HCDR1            FR2
                                         SEQ ID NO:3

Kabat  45                                         66    70    75         80 82ABC
       LEWIGYINPYNDGTKYNEKFKGKATLTSDKSSSTAYMELSSLTS    SEQ ID:NO1
                HCDR2                                 FR3
              SEQ ID NO:4

Kabat  85     90  9394                      105   110
       EDSAVYYCAREGFYYGNFDNWGQGTTLTVSS    SEQ ID:NO1
                  HCDR3                        FR4
                SEQ ID NO:5

FIG. 11B

```
Kabat    1         5         10        15        20                      35        40
         DIQMTQSPASLSASVGETVTITC RASENIYSYLT WYQQKQGKS  SEQ ID NO:2
                    FR1                LCDR1            FR2
                                     SEQ ID NO:6

Kabat    45                    60        65   70   75        80   85
         PQLLVY NAKTLPE GVPSRFSGSGSGTQFSLKINSLQPEDFGSY  SEQ ID NO:2
                LCDR2                      FR3
              SEQ ID NO:7

Kabat                    100   104
         YC QHHYGTPYT FGGGTKLEITR    SEQ ID: NO2
             LCDR3        FR4
           SEQ ID NO:8
```

FIG. 13D

$^{296}$FDQDDWGAWQKFTASAGIQVVGDDLTVTNPKRIAKAVNEKS$^{336}$ SEQ ID NO:49

SEQ ID: 9　　　　SEQ ID: 10

ALPHA-ENOLASE SPECIFIC ANTIBODIES AND METHODS OF USES IN CANCER THERAPY

FIELD OF THE INVENTION

The present invention relates to methods for generation and use of antibodies that bind specifically to the human alpha-enolase protein (ENO1).

BACKGROUND OF THE INVENTION

Tumors result from aberrant, unrestrained proliferation of a single cell, generating a clone of transformed cells. Tumor cells may express unique antigens that can be recognized by the immune system. Tumor-associated antigens include mutated oncogenes, mutated normal cellular proteins, aberrantly expressed cellular proteins, abnormal cell-surface proteins, and oncogenic viral proteins. The immune system views these tumor-associated antigens as non-self and can produce antibodies to eradicate these foreign antigen-bearing tumor cells, while sparing the healthy cells. Therefore, identification of immunogenic tumor-associated antigens may be used as targets for clinical prognostic or therapeutic applications in cancer treatment.

Certain malignancies may be identified by pleural effusion, which is excess fluid in the space between the lung and chest wall. Lung carcinoma, breast carcinoma, and lymphoma cause about 75% of all malignant pleural effusions. Malignant pleural effusion may be enriched with lymphocytic infiltrates and tumor cells. Tumor-associated immune complexes or autoantibodies, such as anti-p53, antinuclear, and anti-L-Myc antibodies, have been found in effusion fluids and are associated with poor prognosis. Several lung tumor-associated antigens have also been identified in malignant effusion, including, cytokeratin 19 fragments, neuron-specific enolase (ENO2), squamous cell carcinoma antigen, and soluble HLA-I, etc.

Alpha-enolase (enolase-1, ENO1) is a multiple functional protein, which was first found as a key enzyme of the glycolysis pathways. Under normal conditions, ENO1 is expressed in the cytosol. However, ENO1 is also found to express on the cell surfaces of many cancer cells as a plasminogen receptor and on activated hematopoietic cells, such as neutrophils, lymphocytes and monocytes. It is known that the up-regulation of plasminogen receptor proteins can induce a cascade response of the urokinase plasminogen activation system (uPAS).

The urokinase plasminogen activator system (uPAS) consists of the urokinase plasminogen activator (uPA), its cognate receptor (uPAR) and two specific inhibitors, the plasminogen activator inhibitor 1 (PAI-1) and plasminogen activator inhibitor 2 (PAI-2). Urokinase plasminogen activator converts plasminogen proenzyme into an active serine protease, plasmin. Plasmin is involved in a number of tissue remodeling processes, such as basement membrane (BM) and extracellular matrix (ECM) remodeling, which is required in tumor progression and metastasis. In addition, it has been shown that the uPAS may be involved in the neoplastic evolution, affecting tumor angiogenesis, malignant cell proliferation, adhesion and migration, intra-vascularization, and growth at the metastatic site.

Specifically, activation of plasminogen can result in extracellular matrix degradations, which in turn can lead to increased metastasis of cancer cells and infiltration of immune cells. In other words, ENO1 expression on cancer cell surfaces as a plasminogen receptor can increase invasion activities of the cancer cells. Therefore, ENO1 is a potential target for cancer therapy.

SUMMARY OF THE INVENTION

Embodiments of the invention relate to targeted binding agents that specifically bind human ENO1, thereby inhibiting ligand (e.g., plasminogen) binding to ENO1. By inhibiting binding of plasminogen to ENO1, targeted binding agents of the invention can inhibit plasminogen activation, leading to reduced degradation of extracellular matrix, which in turn prevents or reduces dissociation of cancer cells from the extracellular matrix. Therefore, targeted binding agents in accordance with embodiments of the invention can be used to inhibit tumor growth and metastasis. Mechanisms by which this can be achieved may include, but are not limited to, inhibition of binding of a ligand (such as plasminogen) to its receptor ENO1, or abrogation of inter-reactions between the receptor ENO1 and its ligands, thereby reducing the effective concentration of ENO1.

In accordance with one embodiment of the invention, a targeted binding agent is an antibody that can bind to human ENO1 to prevent its ligands (e.g., plasminogen) from binding to ENO1. Preventing binding of plasminogen to the receptor can prevent plasminogen activation. This results in the inhibition of the urokinase plasminogen activation system (uPAS) in the extracellular matrix of cancer cells.

In accordance with some embodiments of the invention, the antibody may bind ENO1 with high affinities, such as with a $K_d$ of less than 0.3 nM. Such tight binding agents can inhibit ENO1 with high efficiencies.

In accordance with some embodiments of the invention, a targeted binding agent is an antibody that can bind to human ENO1 and inhibit induced plasmin activity on cancer cells with high efficiencies, such as 80%, 90%, or 100% inhibition. The inhibition assays may be performed by inducing ENO1 expression (hence, plasminogen activation) in a cancer cell (such as U937 human lymphoma cells) by treatment with 10 microgram/mL lipopolysaccharide (LPS) for 5 hours. Inhibition of such induced plasmin activity may be assayed with an antibody at a suitable concentration. Using an antibody of the invention, such inhibition may be detected at antibody concentrations as low as 20 microgram/ml or less.

In accordance with some embodiments of the invention, a targeted binding agent is an antibody that can bind to human ENO1. Such an antibody may be used to inhibit the invasion activity of a cancer cell. For example, antibodies of the invention can inhibit greater than 50%, 60%, or 70% of the invasion activity of human non-small cell lung carcinoma CL1-5 cells at antibody concentrations as low as 50 microgram/ml or less.

In accordance with some embodiments of the invention, a targeted binding agent is an antibody that can bind to human ENO1 to inhibit extracellular matrix degradation, thereby inhibiting cancer cell dissociation from the extracellular matrix. For example, an antibody of the invention can inhibit greater than 40%, 50%, or 60% of plasminogen mediated dissociation of CL1-5 cells from collagen or fibronectin at antibody concentrations as low as 50 microgram/ml or less.

In accordance with embodiments of the invention, a targeted binding agent (i.e. an antibody) may comprise a heavy chain amino acid sequence having a complementarity determining region (CDR) comprising one of the CDR sequences included in sequence 1.

In accordance with some embodiments of the invention, a targeted binding agent (i.e. an antibody) may comprise a light chain amino acid sequence having a complementarity determining region (CDR) comprising one of the CDR sequences included in sequence 2.

In accordance with some embodiments of the invention, a targeted binding agent is an antibody, which may be a monoclonal antibody or a polyclonal antibody.

In accordance with some embodiments of the invention, an antibody that can bind human ENO1 protein comprises a light chain amino acid sequence comprising any one of LCDR1, LCDR2 or LCDR3 sequence included in sequence 2.

In accordance with some embodiments of the invention, an antibody that can bind human ENO1 protein comprises a light chain amino acid sequence comprising any two of LCDR1, LCDR2 or LCDR3 sequence included in sequence 2 (that is, LCDR1 and LCDR2, LCDR1 and LCDR3 or LCDR2 and LCDR3).

In accordance with some embodiments of the invention, an antibody that can bind human ENO1 protein comprises a light chain amino acid sequences that comprises LCDR1, LCDR2 and LCDR3 sequences included in sequence 2. In accordance with certain embodiments of the invention, an antibody may be a humanized antibody or a fully human monoclonal antibody.

In accordance with some embodiments of the invention, an antibody that can bind human ENO1 protein comprises a heavy chain amino acid sequence comprising any one of HCDR1, HCDR2 or hCDR3 sequence included in sequence 1.

In accordance with some embodiments of the invention, an antibody that can bind human ENO1 protein comprises a heavy chain amino acid sequence that comprises any two of HCDR1, HCDR2 or HCDR3 sequence included in n sequence 1 (that is, HCDR1 and HCDR2, HCDR1 and HCDR3 or HCDR2 and HCDR3).

In accordance with some embodiments of the invention, an antibody that can bind human ENO1 protein comprises a heavy chain amino acid sequence that comprises HCDR1, HCDR2 and HCDR3 sequences included in sequence 1. In accordance with some embodiments of the invention, an antibody may be a humanized antibody or a fully human monoclonal antibody.

In accordance with some embodiments of the invention, an antibody that can bind human ENO1 protein comprises a light chain amino acid sequence having a CDR comprising one of the CDR sequences included in sequence 2. In accordance with some embodiments of the invention, an antibody can bind human ENO1 protein and comprises a heavy chain amino acid sequence having a CDR comprising one of the sequences shown in sequences 1. In accordance with some embodiments of the invention, an antibody may be a humanized or a fully human monoclonal antibody.

In accordance with some embodiments of the invention, an antibody that can bind human ENO1 protein comprises a heavy chain amino acid sequence having one of the CDR sequences included in sequence 1 and a light chain amino acid sequence having one of the CDR sequences included in sequence 2. In accordance with some embodiments of the invention, an antibody may be a humanized or a fully human monoclonal antibody.

In accordance with some embodiments of the invention, a targeted binding agent (i.e. an antibody) can compete for binding of plasminogen to human ENO1 protein. In accordance with some embodiments of the invention, said targeted binding agent comprises a heavy chain amino acid sequence having at least one of the CDR sequences included in sequence 1 and a light chain amino acid sequence having at least one of the CDR sequences included in sequence 2.

In accordance with some embodiments of the invention, a targeted binding agent can bind to an epitope comprising the amino acid sequence $^{296}$FD Q D D W G A W Q K F TA$^{309}$ (SEQ ID NO:9) or $^{326}$K R I A K A V N EK S$^{336}$ (SEQ ID NO:10) of human ENO1 protein (GenBank: AAH50642.1). In accordance with some embodiments of the invention, said targeted binding agent comprises a heavy chain amino acid sequence having at least one of the CDR sequences included in sequence 1 and a light chain amino acid sequence having at least one of the CDR sequences included in sequence 2.

In accordance with some embodiments of the invention, a binding agent of the invention may comprise an antigen-binding site within a non-antibody molecule. For example, such a binding agent may comprise one or more CDRs e.g. a set of CDRs in a non-antibody protein scaffold, as discussed further below.

Some embodiments of the invention relate to methods for assaying the level of human ENO1 protein in a patient or a patient sample. A method of the invention comprises contacting an anti-ENO1 antibody with a biological sample from a patient, and detecting the level of binding between said antibody and human ENO1 protein in said sample. In more specific embodiments, the biological sample is blood or plasma.

Other embodiments of the invention relate to compositions comprising a targeted binding agent, which may include an antibody or a functional fragment thereof, and a pharmaceutically acceptable carrier.

Still further embodiments of the invention relate to methods for effectively treating a subject (e.g., human or animal) suffering from an ENO1 disease or disorder. The method may include selecting a subject in need of a treatment for a neoplastic or non-neoplastic disease, and administering to the subject a therapeutically effective dose of an antibody (which may be a humanized or a fully human monoclonal antibody) that specifically binds to ENO1 protein.

The antibody of the invention can be used to treat a human ENO1 protein-related disease or disorder. A human ENO1 protein related disease or disorder may be any condition arising from aberrant activation or expression of human ENO1 protein. Examples of such diseases include where human ENO1 protein aberrantly interacts with its ligands, thereby altering cell-adhesion or cell signaling properties. This alteration in cell adhesion or cell signaling properties can result in neoplastic diseases or some immune diseases.

For example, a human ENO1 protein-related disease may be a neoplastic disease, such as lung, breast, pancreas, liver, colorectal, and prostate cancers.

In accordance with some embodiments of the invention, a targeted binding agent (e.g., an antibody) can bind to the peptide comprising the amino acid sequence $^{296}$FD Q D D W G A W Q K F T$^{308}$ (SEQ ID NO:9) or $^{326}$K R I A K A V N EK S$^{336}$ (SEQ ID NO:10) of human ENO1 protein (GenBank: AAH50642.1) and can be used to treat a human ENO1 protein-related disease or disorder noted above.

Additional embodiments of the invention relate to methods for inhibiting ENO1-induced cell dissociation from extracellular matrix of cancers in a subject. These methods may include selecting a subject (e.g., a human or an animal) in need of treatment for ENO1-induced cell dissociation, and administering to said subject a therapeutically effective dose of an antibody, wherein said antibody specifically binds to ENO1. The antibody may be a humanized or fully human monoclonal antibody.

Further embodiments of the invention relate to the uses of an antibody in the preparation of a medicament for the treatment of an ENO1-related disease or disorder in a subject (e.g., a human or an animal), wherein said antibody specifically binds to ENO1. The antibody may be a humanized or fully human monoclonal antibody.

In accordance with some embodiments of the invention, the targeted binding agents described herein can be used for the preparation of a medicament for the treatment of ENO1 protein-induced cell dissociation from extracellular matrix in an animal, wherein said antibody specifically binds to ENO1. The antibody may be a humanized or fully human monoclonal antibody.

Some embodiments of the invention described herein relate to monoclonal antibodies that bind human ENO1 and affect human ENO1 functions. Other embodiments of the invention relate to anti ENO1 antibody preparations with desirable properties for therapy applications. Such properties may include a high binding affinity for ENO1, the ability to neutralize ENO1 activity in vitro and in vivo, and the ability to inhibit ENO1 induced cell dissociation, growth and metastasis of tumors.

In some embodiments, the invention relates to an antibody that can bind to human ENO1 with very high affinity (i.e., low $K_d$). For example a human, rabbit, mouse, chimeric or humanized antibody that is capable of binding ENO1 with a $K_d$ less than about $10^{-5}$, $10^{-6}$, $10^{-7}$, $10^{-8}$, $10^{-9}$, $10^{-10}$ or about $10^{-11}$ M, or any range or value therebetween. Affinity and/or avidity measurements can be performed using ELISA and/or BIACORE, as described herein or according to techniques known in the art.

It will be appreciated that embodiments of the invention are not limited to any particular form of an antibody or method of generation or production. For example, the anti-ENO1 antibody may be a full-length antibody (e.g., having an intact human Fc region) or an antibody fragment (e.g., a Fab, Fab' or $F(ab')_2$, FV or Dab (Dabs are the smallest functional binding units of human antibodies). In addition, the antibody may be manufactured from a hybridoma that secretes the antibody, or from a recombinantly produced cell that has been transformed or transfected with a gene or genes encoding the antibody.

Other embodiments of the invention relate to isolated nucleic acid molecules encoding any of the antibodies described herein, vectors having isolated nucleic acid molecules encoding anti-ENO1 antibody or a host cell transformed with any of such nucleic acid molecules.

In addition, some embodiments of the invention relate to a method for producing an anti-ENO1 antibody by culturing host cells under conditions wherein a nucleic acid molecule is expressed to produce the antibody, followed by recovering the antibody. It should be realized that embodiments of the invention may also include any nucleic acid molecule which encodes an antibody or fragment of an antibody of the invention including nucleic acid sequences optimized for increasing yields of antibodies or fragments thereof when transfected into host cells for antibody production.

Further embodiments of the invention may relate to methods for producing high affinity antibodies to human ENO1 by immunizing a mammal with human ENO1 protein, a fragment thereof, and one or more orthologous sequences or fragments thereof.

Other embodiments relate to the generation and identification of isolated antibodies that can bind specifically to human ENO1. Inhibition of the biological activity of ENO1 can be effected by these antibodies to prevent ENO1 induced cell dissociation, invasion and other desired effects of cancers.

Other embodiments of the invention relate to pharmaceutical compositions having an effective amount of an anti-ENO1 antibody. The composition may further comprise a pharmaceutically acceptable carrier or diluent. In yet other embodiments, the anti-ENO1 antibody, or a fragment thereof, is conjugated to a therapeutic agent. The therapeutic agent can be, for example, a toxin or a radioisotope.

Yet other embodiments of the invention relate to methods for treating diseases or conditions associated with the expression of ENO1 in a patient. The methods may include administering to a patient an effective amount of an anti-ENO1 antibody. The anti-ENO1 antibody can be administered alone, or can be administered in combination with additional antibodies or chemotherapeutic drug or radiation therapy. For example, a monoclonal, oligoclonal or polyclonal mixture of ENO1 antibody that block cell dissociation can be administered in combination with a drug shown to inhibit tumor cell proliferation directly. The method can be performed in vivo and the patient is preferably a human patient. In a preferred embodiment, the method concerns the treatment of an ENO1-related disease or disorder including, but not limited to, neoplastic diseases, such as lung, breast, pancreas, liver, colorectal, prostate cancers and or solid tumors.

Some embodiments of the invention relate to a method for monitoring cancer development. The method may comprise determining the abundance of alpha-enolase proteins (ENO1) in a sample (e.g., cancer cells), wherein an increased level of ENO1 correlates with cancer severity. In accordance with embodiments of the invention, the abundance may be determined by measuring binding of an ENO1 specific antibody to the ENO1 proteins.

Some embodiments of the invention relate to a method for detecting cancer. Such a method may comprise determining the abundance of ENO1-specific antibodies in serum samples, wherein a low level of ENO1-specific antibodies indicates the presence of a malignant tumor.

BRIEF DESCRIPTION OF THE DRAWINGS

FIG. 7 shows results of inhibition of invasion activities of CL1-5 cells treated with 5 different antibodies isolated from acites of individual hybridomas, respectively. The detailed procedures were described in Example 7. These data show that all 5 different anti-ENO1 antibodies can inhibit the invasion activity of CL1-5 cells. Interestingly, even though clone 8 has a $K_d$ about 7.2-folds higher than that of clone 10, the inhibition of invasion activity against CL1-5 cells by clone 8 is similar to that of clone 10.

FIG. 10C shows results of inhibition of CL1-5 cell dissociation from collagen treated with the EN10 mAb. The cell associated adhesion assay was performed as described in Example 10. These data show that the EN10 mAb inhibits the cell dissociation activity of CL1-5 from collagen in a dose-dependent manner.

FIG. 11A depicts the variable heavy chain region amino acid sequence of EN10 mAb (SEQ ID NO: 1). The framework regions (FR1, FR2, FR3, and FR4) and CDRs (HCDR1, HCDR2, and HCDR3) are indicated. Cloning the EN10 mAb was performed as described in Example 11.

FIG. 11B depicts the variable light chain region amino acid sequence of EN10 mAb (SEQ ID NO: 2). The framework regions (FR1, FR2, FR3, and FR4) and CDRs (LCDR1, LCDR2, and LCDR3) are indicated. Cloning the EN10 mAb was performed as described in Example 11.

FIG. 13D shows the sequences of ENO1 peptide 1 (FD Q D D W GA W Q K F TA (SEQ ID NO: 9)) and peptide 2 (K R I A K A V N EK S (SEQ ID NO:10)) between amino residue number 296 and 336 of human ENO1 (SEQ ID NO:49), which participate in human ENO1 and EN10 mAb binding.

DEFINITIONS

Figure 1:
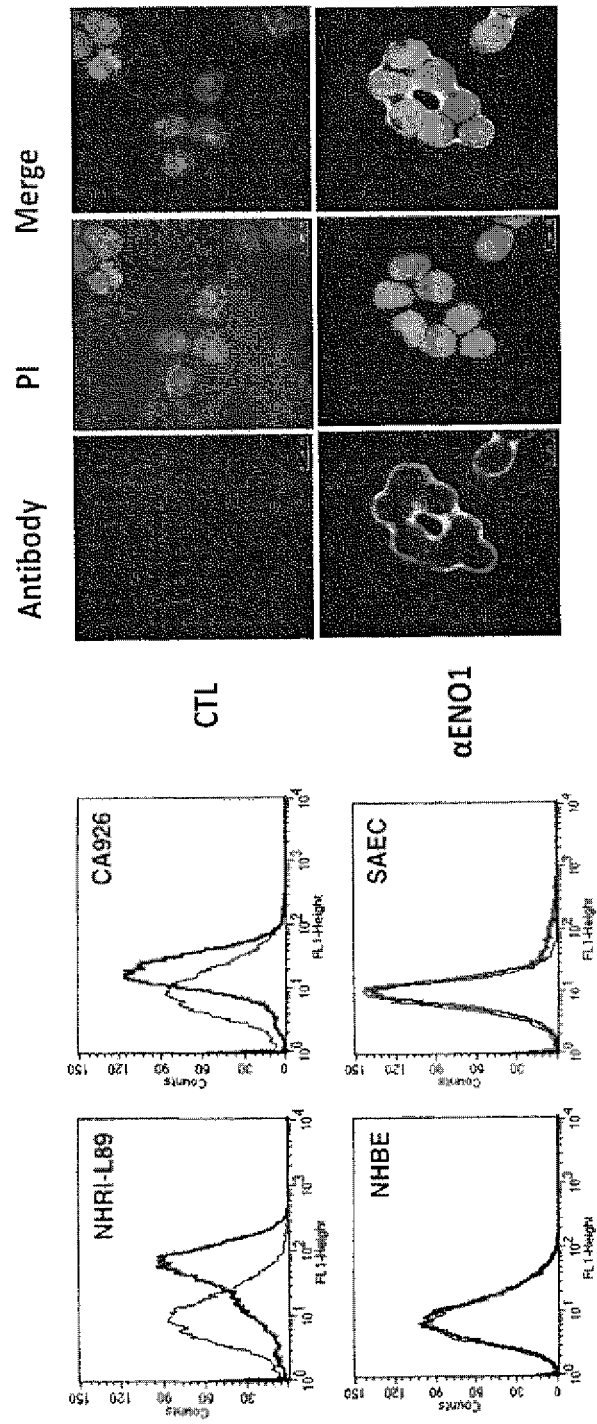
FIGS. 1A and 1B show results from studies of cell surface location of ENO1 in malignant cells using flow cytometry (FIG. 1A) and immunostaining (FIG. 1B), respectively. Detailed procedures were performed as described in Example 1. The data show that ENO1 is located on cell surface in malignant cells (NHRI-L89 & CA926), but not in normal lung epithelial cells (NHBE & SAEC).

Unless otherwise defined, scientific and technical terms used herein shall have the meanings that are commonly understood by those of ordinary skill in the art. Furthermore, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings: The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

An antagonist may be a polypeptide, nucleic acid, carbohydrate, lipid, small molecular weight compound, an oligonucleotide, an oligopeptide, interference RNA (RNAi), antisense, a recombinant protein, an antibody, or conjugates or fusion proteins thereof. For a review of RNAi, see Milhavet O, Gary D S, Mattson M P. (Pharmacol Rev. 2003 December; 55(4):629-48. Review.) and for antisense approach, see Opalinska J B, Gewirtz A M. (Sci STKE. 2003 Oct. 28; 2003 (206): pe47).

Disease-related aberrant activation or expression of "ENO1" may be any abnormal, undesirable or pathological cell adhesion, for example tumor-related cell adhesion. Cell adhesion-related diseases include, but are not limited to, non-solid tumors such as leukemia, or lymphoma, and also solid tumors such as melanoma, non-small cell lung cancer, hepatocellular (liver) carcinoma, gastric, head and neck, hepatic system, stomach, breast, ovary, lung, lung, uterus, vulva, colorectum, and pancreas.

The term ENO1 refers to the heterodimer enolase molecule consisting of an ENO1 and ENO2 or ENO3.

As used herein, the term "antibody" refers generally and broadly to immunoglobulins, autoantibodies, monoclonal antibodies, and polyclonal antibodies, as well as active fragments thereof. The fragment may be active in that it binds to the cognate antigen, or it may be active in that it is biologically functional. The antibodies of the invention may be chimeric, humanized, or human, using techniques known in the art.

As used herein, the term "monoclonal antibody" refers to antibodies that are chemically and immunologically homogeneous, generally produced by hybridomas. See A Laboratory Manual, Harlow and Lane, eds., Cold Spring Harbor, N.Y. (1988).

As used herein, the term "polyclonal antibody" refers to antibodies that are produced by more than one clone of antibody-synthesizing plasma cells (B-lymphocytes) in response to the same antigen. They are generally produced by the animal after it is immunized with the antigen.

As used herein, the term "chimeric antibody" refers to antibodies that contain sequences from more than one source. For example, such antibodies may contain sequences from non-human sources that are then modified by introducing human sequences. As used herein, the term "humanized antibody" refers to an antibody in which minimal portions of a non-human antibody are introduced into an otherwise human antibody. As used herein, the term "human antibody" refers to an antibody in which substantially every part of the protein is substantially non-immunogenic in humans, with only minor sequence changes or variations.

As used herein, the term "alpha-enolase specific antibody" refers to an antibody that has a high specificity for mammalian ENO1, but not to ENO2 or ENO3. Similarly, the term "ENO1-specific antibody" refers to an antibody that binds the alpha-enolase protein.

The term "neutralizing" when referring to a targeted binding agent, such as an antibody, relates to the ability of said targeted binding agent to eliminate, or significantly reduce, the activity of a target antigen. Accordingly, a "neutralizing" ENO1 antibody is capable of eliminating or significantly reducing the activity of ENO1. A neutralizing ENO1 antibody may, for example, act by blocking the binding of ENO1 to the plasminogen. By blocking this binding, the plasminogen mediated cell dissociation is significantly, or completely, eliminated. Ideally, a neutralizing antibody against ENO1 enhances cell adhesion.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "CDR region" or "CDR" is intended to indicate the hypervariable regions of the heavy or light chains of the immunoglobulin as defined by Kabat et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids, although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974).

The term a "set of CDRs" referred to herein comprises CDR1, CDR2 and CDR3. Thus, a set of HCDRs refers to HCDR1, HCDR2 and HCDR3 (HCDR refers to a variable heavy chain CDR), and a set of LCDRs refers to LCDR1, LCDR2 and LCDR3 (LCDR refers to a variable light chain CDR). Unless otherwise stated, a "set of CDRs" includes HCDRs and LCDRs.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity.

The terms "substantial identity" or "substantially identical" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least about 75%, more preferably at least 80%, 90%, 95%, and most preferably about 99% sequence identity to the antibodies or immunoglobulin molecules described herein. In particular, conservative amino acid replacements are contemplated.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxyl-termini of fragments or analogs occur near boundaries of functional domains. Structural and functional domains can be identified by comparison of the nucleotide and/or amino acid sequence data to public or proprietary sequence databases. Methods to identify protein sequences that fold into a known three-dimensional structure are known. Bowie et al., (1991) Science 253:164. Thus, the foregoing examples demonstrate that those of skill in the art can recognize sequence motifs and structural conformations that may be used to define structural and functional domains in accordance with the antibodies described herein.

A further aspect of the invention is a targeting binding agent or an antibody molecule comprising a VH domain that has at least about 60, 70, 80, 85, 90, 95, 98 or about 99% amino acid sequence identity with a VH domain of any of antibodies shown in sequences 1, the appended sequence listing, an antibody described herein, or with an HCDR (e.g., HCDR1, HCDR2, or HCDR3) shown in sequences 1. The targeting binding agent or antibody molecule may optionally also comprise a VL domain that has at least about 60, 70, 80, 85, 90, 95, 98 or about 99% amino acid sequence identity with a VL domain any of antibodies shown in sequences 2, the appended sequence listing, an antibody described herein, or with an LCDR (e.g., LCDR1, LCDR2, or LCDR3) shown in sequences 2. Algorithms that can be used to calculate % identity of two amino acid sequences comprise e.g. BLAST (Altschul et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters. In some embodiments, the targeting binding agent or antibody that shares amino acid sequence identity as describes above, exhibits substantially the same activity as the antibodies referenced. For instance, substantially the same activity comprises at least one activity that differed from the activity of the references antibodies by no more that about 50%, 40%, 30%, 20%, 10%, 5%, 2%, 1% or less.

An antigen binding site is generally formed by the variable heavy (VH) and variable light (VL) immunoglobulin domains, with the antigen-binding interface formed by six surface polypeptide loops, termed complementarity determining regions (CDRs). There are three CDRs in each VH (HCDR1, HCDR2, HCDR3) and in each VL (LCDR1, LCDR2, LCDR3), together with framework regions (FRs).

Typically, a VH domain is paired with a VL domain to provide an antibody antigen-binding site, although a VH or VL domain alone may be used to bind antigen. The VH domain (e.g. from sequence 1) may be paired with the VL domain (e.g. from sequence 2), so that an antibody antigen-binding site is formed comprising both the VH and VL domains. Analogous embodiments are provided for the other VH and VL domains disclosed herein. In other embodiments, VH chains in sequences 1 are paired with a heterologous VL domain. Light-chain promiscuity is well established in the art. Again, analogous embodiments are provided by the invention for the other VH and VL domains disclosed herein. Thus, the VH of the parent or of any of antibodies chain on sequences 2 may be paired with the VL of the parent or of any of antibodies on sequences 1, and 2 or other antibody.

An antigen binding site may comprise a set of H and/or L CDRs of the parent antibody or any of antibodies in sequences 1 and 2 with as many as twenty, sixteen, ten, nine or fewer, e.g. one, two, three, four or five, amino acid additions, substitutions, deletions, and/or insertions within the disclosed set of H and/or L CDRs. Such modifications may potentially be made at any residue within the set of CDRs.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutant proteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

A further aspect of the invention is an antibody molecule comprising a VH domain that has at least about 60, 70, 80, 85, 90, 95, 98 or about 99% amino acid sequence identity with a VH domain of any of antibodies listed in sequences 1, the appended sequence listing or described herein, or with an HCDR (e.g., HCDR1, HCDR2, or HCDR3) shown in sequence 1. The antibody molecule may optionally also comprise a VL domain that has at least 60, 70, 80, 85, 90, 95, 98 or 99% amino acid sequence identity with a VL domain of any of the antibodies shown in sequences 2, the appended sequence listing or described herein, or with an LCDR (e.g., LCDR1, LCDR2, or LCDR3) shown in sequence 2. Algorithms that can be used to calculate % identity of two amino acid sequences comprise e.g. BLAST, FASTA, or the Smith-Waterman algorithm.

Variants of the VH and VL domains and CDRs of the present invention, including those for which amino acid sequences are set out herein, and which can be employed in targeting agents and antibodies for human ENO1 protein can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate complex; ability to bind to a specified epitope; linear epitope, e.g. peptide sequence identified using peptide-binding scan as described herein, e.g. using peptides screened in linear and/or constrained conformation; conformational epitope, formed by non-continuous residues; ability to modulate a new biological activity of human ENO1 protein or downstream molecule. Such methods are also provided herein.

A further aspect of the present invention relates to a targeted binding agent (i.e. an antibody) including those for which amino acid sequences that binds to the epitope peptide comprising amino acid sequence that has at least about 60, 70, 80, 85, 90, or about 92% amino acid sequence identity listed in sequences 9 or 10 on human ENO1 protein and can be used to treat an human ENO1 protein disease or disorder. A human ENO1 protein-related disease or disorder can be any condition arising due to the aberrant activation or expression of human ENO1 protein. In one example, the human ENO1 protein-related disease is a neoplastic disease such as non-small cell lung cancer, hepatocellular (liver) carcinoma, gastric (stomach) cancer, breast cancer, pancreatic duct adenocarcinoma.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

The techniques required to make substitutions within amino acid sequences of CDRs, antibody VH or VL domains and/or binding agents generally are available in the art. Variant sequences may be made, with substitutions that may or may not be predicted to have a minimal or beneficial effect on activity, and tested for ability to bind and/or neutralize and/or for any other desired property. Variable domain amino acid sequence variants of any of the VH and VL domains whose sequences are specifically disclosed herein may be employed in accordance with the present invention, as discussed.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least about 5, 6, 8 or 10 amino acids long, preferably at least about 14 amino acids long, more preferably at least about 20 amino acids long, usually at least about 50 amino acids long, and even more preferably at least about 70 amino acids long. The term "analog" as used herein refers to polypeptides which are comprised of a segment of at least about 25 amino acids that has substantial identity to a portion of a deduced amino acid sequence and which has at least one of the following properties: (1) specific binding to human ENO1 protein under suitable binding conditions, (2) ability to block appropriate ligand/ENO1 protein binding, or (3) ability to inhibit ENO1 protein activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

As used herein, a "targeted binding agent" is an agent, e.g. antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain of an antibody, wherein said domain is fused or contained within a heterologous protein.

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. The term antibody also includes binding fragments of the antibodies of the invention; exemplary fragments include Fv, Fab, Fab', single stranded antibody (svFC), dimeric variable region (Diabody) and disulfide stabilized variable region (dsFv). "Binding fragments" of an antibody may be produced by recombinant DNA techniques, or by enzymatic or chemical cleavage of intact antibodies. Binding fragments include Fab, Fab', F(ab')$_2$, Fv, and single-chain antibodies.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CH1 domain of the heavy chain. The term "mAb" refers to monoclonal antibody.

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≤1 micro M, preferably ≤100 nM, and most preferably ≤10 nM.

"Active" or "activity" in regard to an ENO1 polypeptide refers to a portion of an ENO1 polypeptide that has a biological or an immunological activity of a native ENO1 polypeptide. "Biological" when used herein refers to a biological function that results from the activity of the native ENO1 polypeptide. A preferred ENO1 biological activity includes, for example, ENO1 induced the plasminogen activity.

"Mammal" when used herein refers to any animal that is considered a mammal. Preferably, the mammal is human. The term "subject" includes human and veterinary subjects.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, the term "monitoring" refers to the process of detecting and/or observing the development of cancer by determining the abundance of ENO1 protein in cancer cells.

Methods for determining the abundance of ENO1 include, but are not limited to, measuring the binding of ENO1 proteins and ENO1-specific antibodies, Western blotting, flow cytometry, immunohistochemistry (IHC), RT-PCR, and/or microarray analysis.

EXAMPLES

The practice of the present invention will employ technologies comprising conventional techniques of cell biology, cell culture, antibody technology, and genetic engineering, which are within the ordinary skills of the art. Such techniques are explained fully in the literature.

The following examples illustrate the development and use of ENO1-specific antibodies to suppress tumor growth by inducing an anti-ENO1 immune response.

Example 1

Cell Surface Location of ENO1 in Malignant Cells

To analyze the cell location of ENO1 on the malignant cells, the flow cytometry was performed to confirm the cell-surface localization of ENO1. Tumor cells were obtained from pleural effusions of 17 patients with lung cancer. Among them, tumor cells obtained from 2 cancer patients, NHRI-L89 and CA926 effusion tumor cells, are representative cases shown here. NHBE and SAEC cells are normal human lung primary cells. Intact whole cells were stained with or without ENO1 antiserum and analyzed for the surface ENO1 distribution using the antibody specific to ENO1 protein in flow cytometric analysis (as shown in FIG. 1A). The cell localization of ENO1 of lung cancer cell line NHRI-L89 is further confirmed by immunohistology (FIG. 1B). Briefly, $1 \times 10^4$ of NHRI-L89 cells were grown in DMEM containing 10% FCS on a chamber slide coated with fibronectin. After overnight culture, the slide was washed with PBS and blocked with goat serum for 1 hour. NHRI-L89 intact whole cells were stained with control (CTL) or ENO1 antibody for surface ENO1, followed by PI staining for nuclear detection. The stainings were visualized under a confocal microscope (400×; FIG. 1B).

The results of this study are shown in FIGS. 1A (flow cytometry) and 1B (immunostaining). Incubating NHRI-L89 and CA926 with ENO1 antibody shifts the histogram to the right, as compared to incubating the cells with control antibody. Normal NHBE and SAEC human lung primary cells show no significant shifts (FIG. 1A). This result indicates that the ENO1 protein is expressed on the lung cancer cells, but not on normal primary cells (FIG. 1A). When the cell localization of ENO1 was further analyzed by immunohistology, intact NHRI-L89 cells stained with ENO1 antibody shows the signals on the cell surface (FIG. 1B). This result suggests that ENO1 is expressed on the surface of lung and some cancer cells and, therefore, can be a potential target for immune therapy.

Example 2

Anti-ENO1 Antibody Inhibits the Invasion Capacity of Human Lung Cancer Cells

To investigate the effects of ENO1 antibody on cancer cell invasion, the invasion activity of the CL1-5 cells was assessed using a Transwell assay by adding ENO1 antibody to CL1-5 cells grown on micropore filters (Becton Dickinson, Franklin Lakes, N.J.) coated with extracellular matrix (matrigel) (Becton Dickinson). After being mixed with 1:20, 1:100, and 1:500 dilutions of anti-ENO1 polyclonal antibody, respectively, $2 \times 10^4$ cells of CL1-5 were seeded in the top chamber with media containing 2% FBS of a two-chamber assay system and incubated for 24 hours with 10% FBS medium in the lower chamber. An anti-GST mouse polyclonal antibody was used as a negative control group. Two chambers were separated by a micropore filter (12 micrometer pore size) coated with matrigel. After the incubation period, the matrigel-coated filters were stained and the number of cells invading into the matrigel-coated filter was quantified under a microscope. The study was repeated three times. Data are presented as mean±SD. The test was used to compare activity between each group. The P values <0.05 were considered statistically significant.

Figure 2:
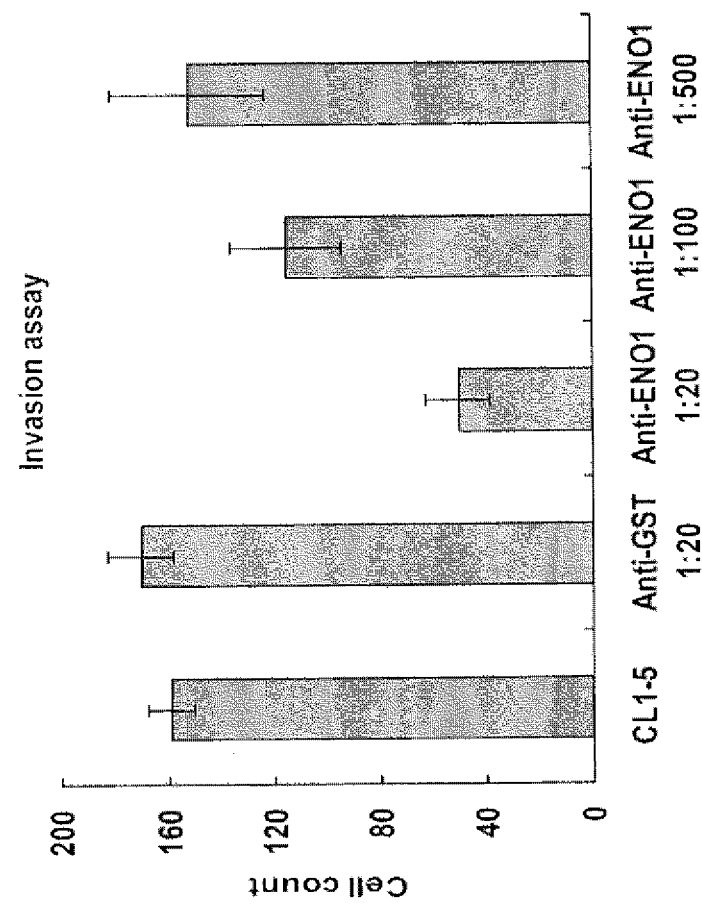
FIG. 2 shows the inhibition of invasion activity of highly-invasive CL1-5 lung adenocarcinoma cells by polyclonal antibody against cell-surface ENO1. Detailed procedures were performed as described in Example 2. The data show that administrating anti-ENO1 polyclonal antibody attenuates the invasion of CL1-5.

The results are shown in the FIG. 2. There are no significant cell count difference between the non-treated (160±8; N=3) and the anti-GST polyclonal treated group (168±12; N=3). However, when CL1-5 cells were administrated with different dilutions of ENO1 polyclonal antibody, cell counts of CL1-5 are reduced, ranging from 52±12 (N=3) for the 1:20 dilution to 156±30 (N=3) for the 1:500 dilution; the reduction is proportional to the concentrations of ENO1 polyclonal antibody. There is statistics cell count difference between the 1:20 dilution of ENO1 polyclonal and 1:20 dilution of anti-GST polyclonal groups (P<0.05). These results suggest that the administration of ENO1 antibody to CL1-5 cancer cells inhibits the cell invasion activity in vitro.

Example 3

ENO1 Polyclonal Antibody Attenuates the Tissue Invasion Capability of CL1-5F4 Cells in Lung To investigate the effect of administration of ENO1 antibody on metastasis of lung cancer cells and evaluate the potential of anti ENO1 antibody in cancer therapy, highly-invasive CL1-5F4 cells with a luciferase reporter gene ($1 \times 10^6$ cells/mouse) were intravenously injected into NOD-SCID mice, together with an ENO1 antibody or a control (CTL) antiserum twice per week. The lung metastatic colony formation was monitored 12 and 19 days after tumor injection using an IVIS system. The mouse injected with CL1-5F4 cells with knockdown of ENO1 gene was used as a negative control. After the mice were scarified on days 12 and 19, the metastatic colonies and tumor sizes were visualized and counted.

Figure 3:
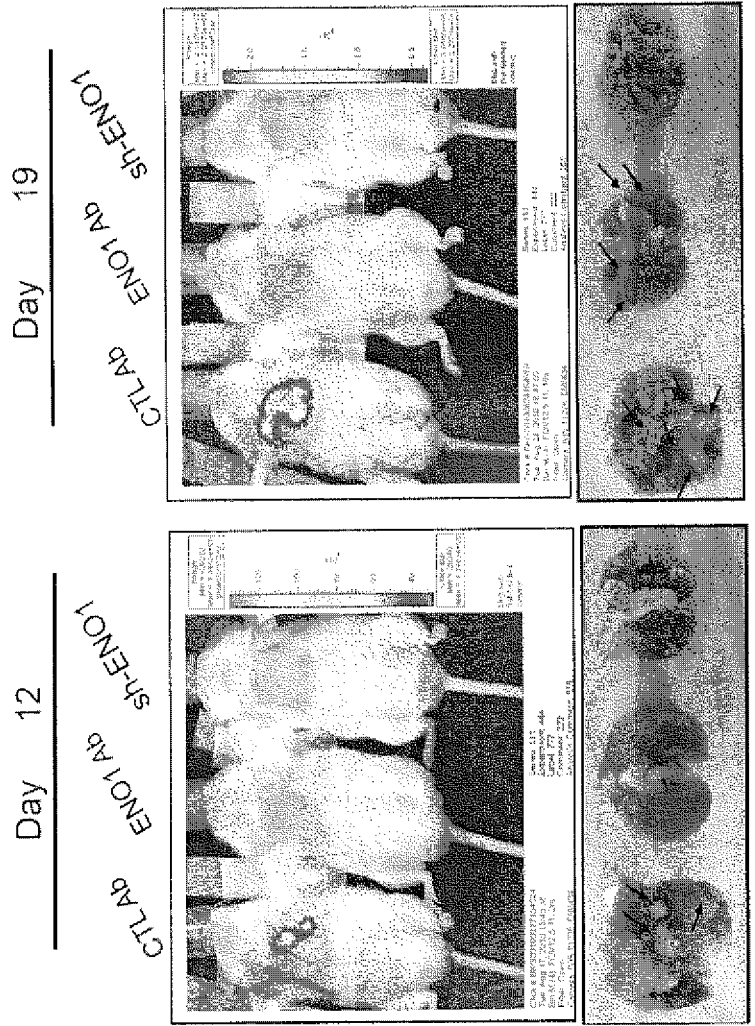
FIG. 3 shows that a polyclonal antibody against human ENO1 attenuates tissue invasion capability of CL1-5F4 cells in lung. The administration of antibody in an animal and the lung metastatic colony formation was monitored 12 and 19 days after tumor injection using an IVIS system. The detailed procedures were performed as described in Example 3. The data show that ENO1 polyclonal antibody inhibits the migration of CL1-5F4 to lung in vivo.

The results are shown in FIG. 3. When a mouse bearing CL1-5F4 cells with a luciferase reporter gene was administrated with a control antibody, the lung of mouse started to show fluorescence signals on day 12. On the other hand, signals were not detected in the mouse treated with ENO1 polyclonal antibody or in the mouse bearing CL1-5F4 cells and having knockdown of ENO1 gene. On the day 19, the signal of mouse treated with control antibody appeared stronger, indicating the presence of more cell invasion or tumor growth. On the same day, signals were still not detected in the mouse treated with ENO1 polyclonal antibody or in the mouse bearing CL1-5F4 cells with knockdown of ENO1 gene. These results indicate that the metastasis of CL1-5F4 cells was compromised by ENO1 antibody or ENO1 gene knock-down (FIG. 3; Top panel). After days 12 and 19, lungs of each treatment group were removed and tumor nodules were determined. The results are shown in the bottom panels in FIG. 3. There are a few tumor nodules appearing in the control anti-body treatment mouse with clear tumor sizes. However, the mouse treated with ENO1 polyclonal antibody or mouse bearing CL1-5F4 ENO1 knockdown showed no clear tumor nodules, indicating the delay of tumor metastasis in these two groups of mice. The results of this study suggest that administrating ENO1 antibody has anti-metastasis or anti-proliferation effects on cancer cells in vivo and ENO1 antibody has potential applications in cancer therapy.

Example 4

The Generation of Anti-Human ENO1 Monoclonal Antibody

From examples 2 and 3, it is clear that ENO1 antibody can attenuate the invasion and metastasis of cancer cells. Therefore, ENO1 antibody can potentially be developed as a therapeutic antibody. To generate a monoclonal antibody against human ENO1, BALB/c mice were primed with purified recombinant human ENO1 antigen (50 μg/mouse), followed by boosting the ENO1 humoral responses with an emulsified CpG adjuvant. The splenocytes were harvested, fused with Fo cells, and then diluted according to a standard protocol. The hybridoma cells secreting monoclonal antibodies that recognize the ENO1 antigen were selected by an antigen-based ELISA. The selected clones were then verified by the binding activity of the antibodies to the cell-surface ENO1 on CL1-

5F4 lung adenocarcinoma cells, using intact whole cell staining in flow cytometric analysis, as described in Example 1.

Figure 4:
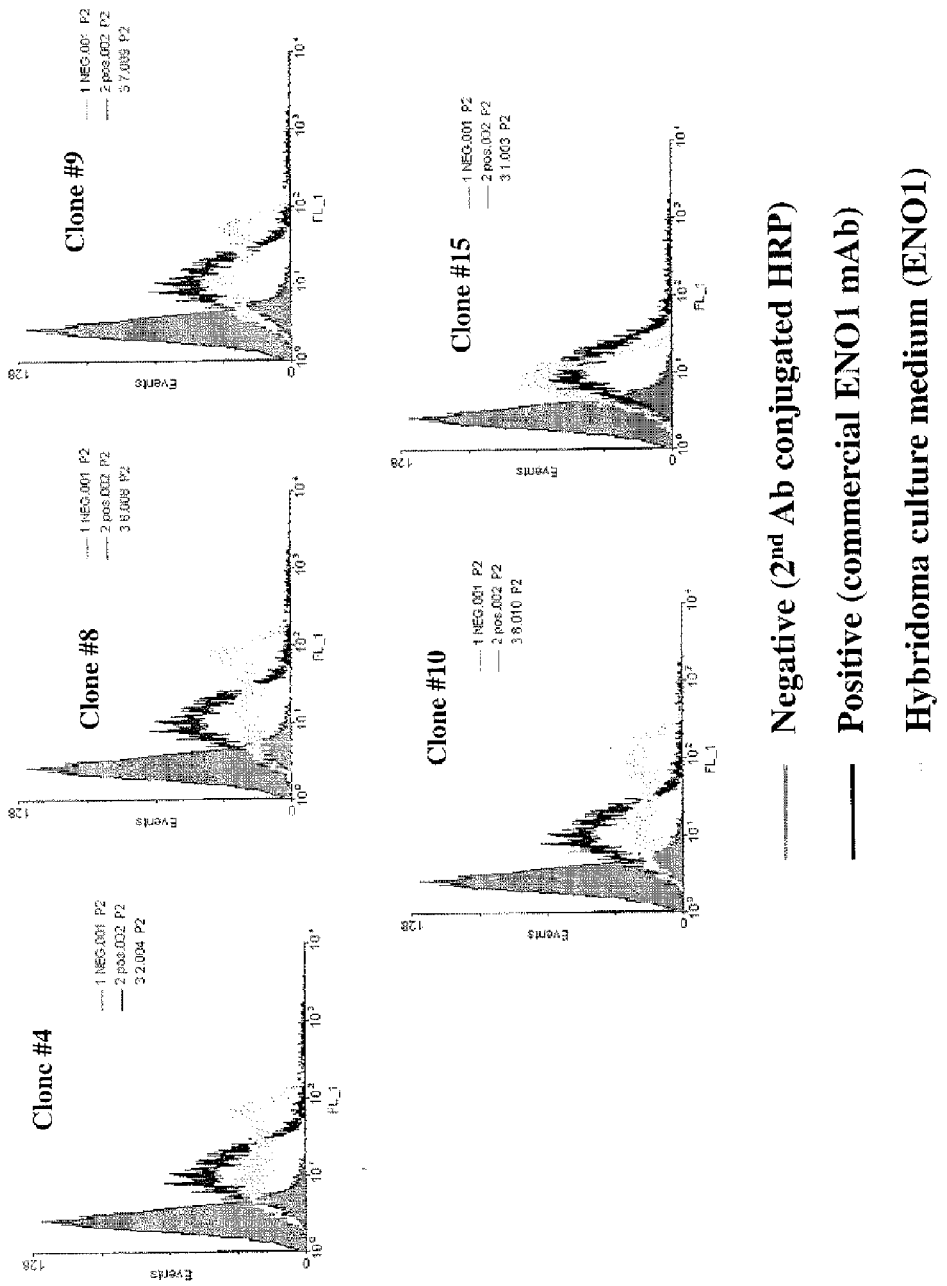
FIG. 4 shows the generation of anti-ENO1 antibody hybridomas and verification of each monoclonal antibody clones by flow cytometry. The procedures for the immunization of mice and generation of hybridoma, and the production of each antibody and verification of antibody by flow cytometry were described in Example 4. The data show that all 5 hybridoma antibodies recognize the surface ENO1 on the CL1-5F4 lung adenocarcinoma cells.

The results are shown in the FIG. 4. All of five antibody clones isolated recognize the cell surface ENO1 on CL1-5F4, as evidenced by the histograms shifting to right, as compared with the control antibody.

Example 5

The ENO1 Binding ELISA of 5 Antibody Clones Isolated

To investigate the ENO1 binding affinities of 5 antibody clones isolated above, the individual hybridomas were grown in RPMI containing 10% FCS. After one week culture $1\times10^6$ cells were collected, washed with PBS, resuspended in 200 ul RPMI medium, and injected to a SCID mouse by IP injection. After 3 weeks, acities of mouse was collected and diluted to 15 ml. Antibody was further purified by 40% ammonium sulfate precipitation and a Protein A column (Montage antibody purification kit Millipore). The purified antibody was concentrated with an Amicon Ultra-15 centrifugal filter device, following the protocols provided by manufacturer (Millpore). The purities of the antibodies were analyzed by 12% SDS PAGE. Human ENO1 protein (400 ng) was coated on a 96-well ELISA plate and the plate was washed with PBS twice. A series of dilutions from $1\times10^{-11}$ to $1\times10^{-7}$ M of individual antibodies were added to the plate, and the plate was incubated at 37° C. for 1 hour. A goat anti mouse IgG conjugated with HPRT was added and after 1 hour incubation, and then TMB was added. The OD405 was read to calculate the activity. Every study was repeated three times, and the data were presented as mean±SD. OD readings and concentrations of antibodies were used to make a multiple scatter plot using Sigmaplot™. The $K_d$ values of clones were predicted by four parameter logistic fit.

Figure 5:
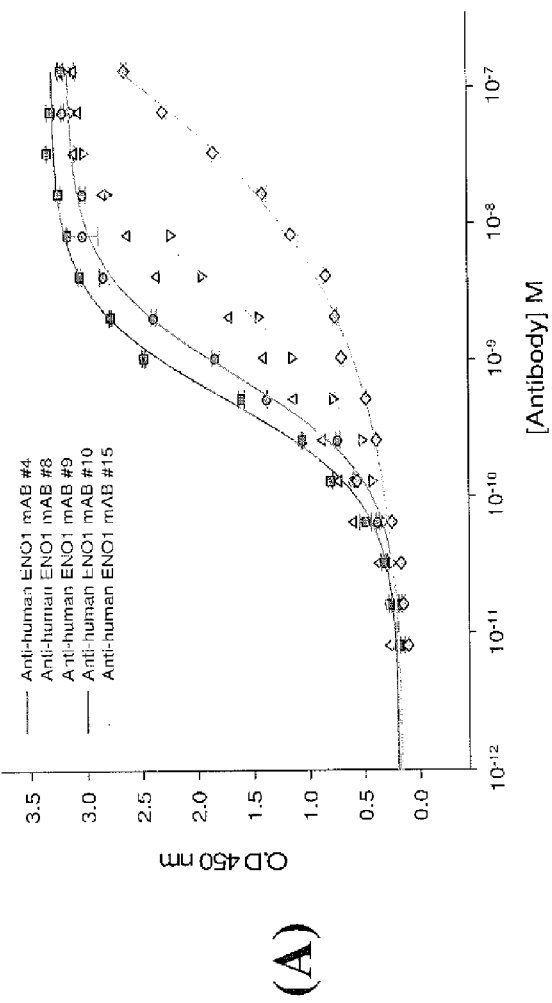
FIG. 5A shows ENO1 binding in ELISA of 5 antibodies isolated from acites of individual hybridomas. Ammonium sulfate purification, protein A column purification, and SDS-PAGE purification were performed as described in Example 5. The data in FIG. 5B show the $K_d$ values of 5 different anti human ENO1 antibodies.

The results of this experiment are shown in FIG. 5. All of antibody hybridomas have productivities from 20.4 mg to 4.6 mg per mice. The $K_d$ values of the antibodies range from $3.77\times10^{-10}\pm0.12$ to $1.6\times10^{-5}\pm0.2$ M (N=3). These results suggest that these 5 antibody clones recognize the human ENO1 protein and that clone 10 has the best affinity with a $K_d$ of about $1.77\times10^{-10}\pm0.12$ M (N=3).

Example 6

The Plasminogen Receptor Antagonist Activities of 5 Antibody Clones Isolated

To study the ENO1 antagonist activities of an isolated anti-human ENO1 antibody, a U937 human lymphoma cell line was grown in RPMI containing 10% FCS. Cells were treated with 10 microgram/ml of LPS for 6 hours to induce ENO1 protein expression on the cell surface. $1.5\times10^6$ cells/ml in PBS were pre-incubated with 1 microgram/ml of human Lys-plasminogen and 10 microgram/ml of different clones of anti ENO1 antibodies for one hour, respectively. Samples were washed with PBS twice, and then 3 nM of tissue specific plasminogen activator and 0.5 mM of chromogenic substrate S-2251 were added. After one hour incubation at 37° C., the OD405 was read to calculate the activities. Each study was repeated three times, and the antagonist activities were analyzed. Data are presented as mean±S D. T-test was used to compare activity between each group. P values <0.05 were considered statistically significant.

Figure 6:
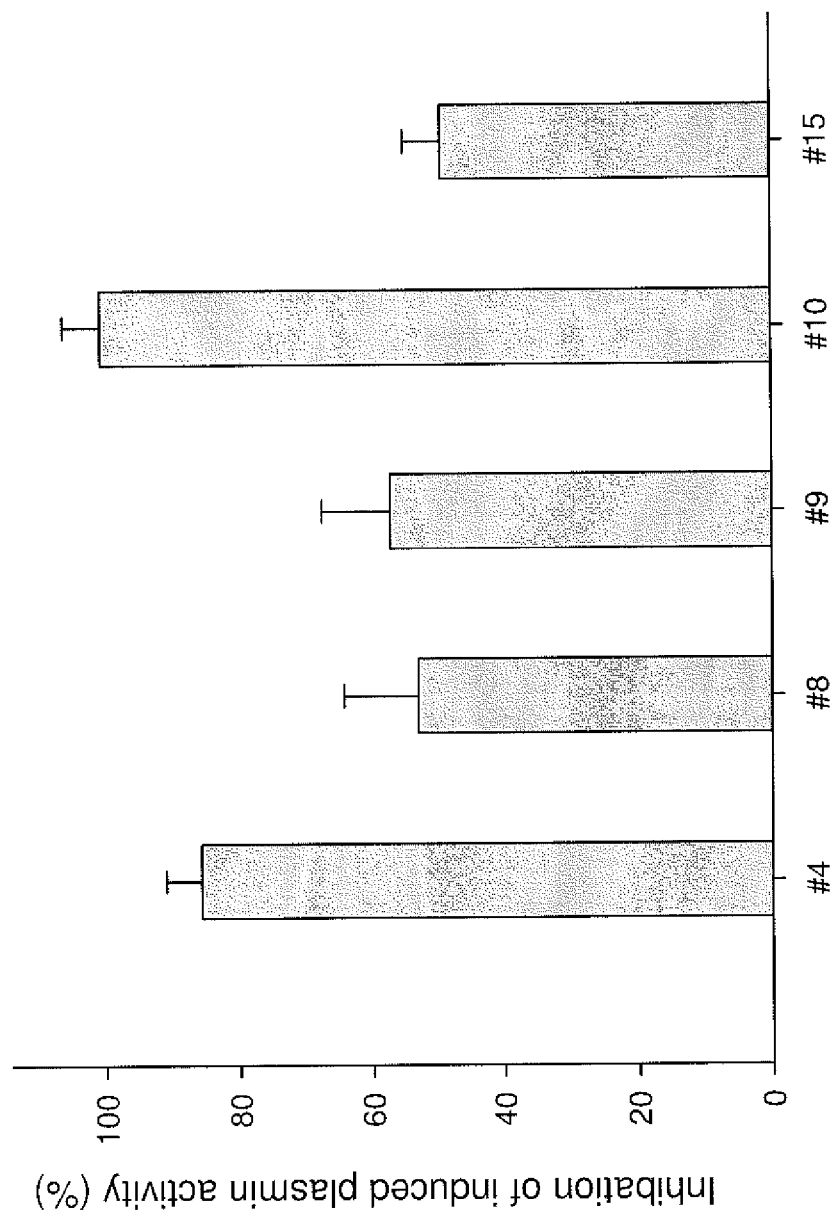
FIG. 6 shows the results of U937 fibrinolytic assay of 5 antibodies isolated from acites of individual hybridomas, respectively. The induction of ENO1 expression by LPS in human U937 lymphoma cell line and the plasmin activity assay were performed as described in Example 6. These data also show that 5 different anti-ENO1 antibodies have different inhibition activities against plasminogen receptor of ENO1 and that the inhibition activities correlate with the $K_d$ values.

Results of this study are shown in FIG. 6. All of 5 clone antibodies have plasminogen receptor antagonist activities with inhibition, ranging from 52% to 100% of LSP-induced ENO1 specific activity. These studies suggest that the plasminogen receptor antagonist activity is proportional to the $K_d$ value of each clone, and that clone 10 has the best inhibition activity, close to 100% inhibition of ENO1 specific activity induced by LPS.

Example 7

ENO1 Monoclonal Antibody Inhibits the Invasion Capacity of Human Lung Cancer Cells The inhibition of the invasion capacity of CL1-5 cells by each antibody clone was assessed using a Transwell assay using micropore filters (Becton Dickinson, Franklin Lakes, N.J.) coated with extracellular matrix (matrigel) (Becton Dickinson). After mixing with 10 microgram/ml each of 5 clone antibodies, $2\times10^4$ cells were seeded in the top chamber of a two-chamber assay system and incubated for 24 hours with media containing 10% FBS in the lower chamber. An anti-mouse IgG and 5-aza-2-deoxy cytidine (5ADC) were used as a negative control and a positive control, respectively. Two chambers were separated by a micropore filter (12 micron pore size) coated with matrigel. After the incubation period, the matrigel-coated filters were stained and the number of cells invading into the matrigel-coated filter was quantified under a microscope. Each study was repeated three times. Data were presented as mean±SD. T-test was used to compare activity between each group. P values <0.05 were considered statistically significant.

Results from these experiments are shown in FIG. 7. These results show that all anti-human ENO1 antibody clones have inhibitory activities against the invasion capacity of CL1-5, and that clone 10 has the best inhibition activity, about $65.5\pm0.3\%$ (N=3) of the control IgG group.

Taking together the results from Examples 5, 6, and 7, anti-human ENO1 antibody clones 10 was chosen for further development and referred to as EN10 mAb in this description.

Example 8

EN10 mAb Inhibits the Invasion Capacity of Human Lung Cancer Cells and Lymphoma Cells The inhibition of the invasion capacity of CL1-5 cells by EN10 mAb was assessed using a Transwell assay using micropore filters (Becton Dickinson, Franklin Lakes, N.J.) coated with extracellular matrix (matrigel) (Becton Dickinson). After mixing with 10, 50, and 100 microgram/ml of EN10 mAb, respectively, $2\times10^4$ cells were seeded in the top chamber with media containing 2% FBS in a two-chamber assay system and incubated for 24 hours with 10% FBS medium in the lower chamber. An anti-mouse IgG was used as a negative control. Two chambers were separated by a micropore filter (12 μm pore size) coated with matrigel. After the incubation period, the matrigel-coated filters were stained, and the number of cells invading into the matrigel-coated filter was quantified under a microscope. Each study was repeated three times. Data are presented as mean±SD. T-test was used to compare activities between each group. P values <0.05 are considered statistically significant. The results are shown in FIG. 8A.

Similarly, inhibition of the invasion capacity of U937 cells by EN10 mAb was assessed using a Transwell assay using micropore filters (Becton Dickinson, Franklin Lakes, N.J.) coated with extracellular matrix (matrigel) (Becton Dickinson). A human lymphoma U937 cell line was grown in RPMI containing 10% FCS. Cells were treated with 10 microgram/ml of LPS for 6 hours to induce ENO1 protein expression on cell surface. After mixing with 10, 50, and 100 microgram/ml of EN10 mAb, respectively, $2\times10^4$ cells were seeded in the top chamber of a two-chamber assay system and incubated for 24 hours with media containing 10% FBS and 10 nM MCP-1 in the lower chamber. An anti-mouse IgG was used as a negative control. Two chambers were separated by a micropore filter (8 μm pore size) coated with matrigel. After the incubation period, cell in the lower chamber were counted by a hemocytometer under a microscope. Each study was repeated three times. Data were presented as mean±SD. T-test was used to compare activity between each group. P values <0.05 are considered statistically significant.

Figure 8A:
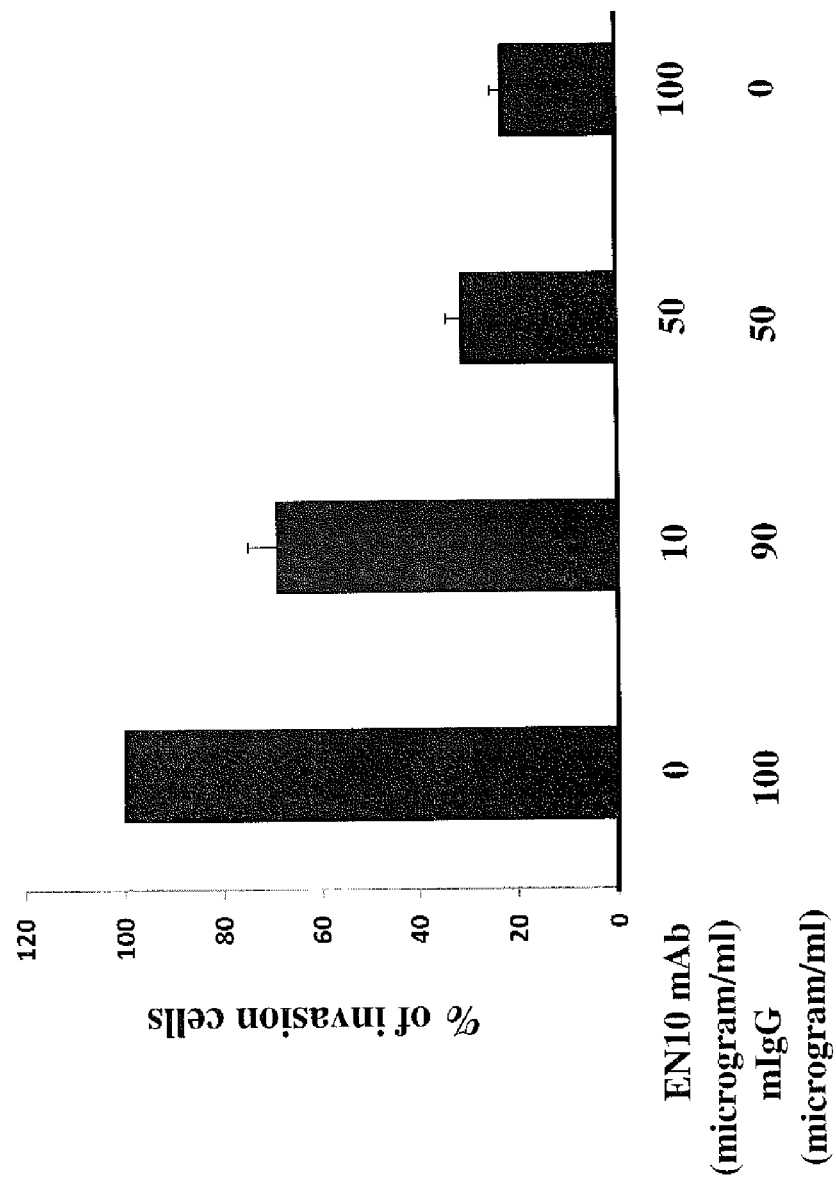
FIG. 8A shows results of invasion activities of CL1-5 cells treated with different concentrations of EN10 mAb isolated from hybridoma. Detailed procedures were performed as described in Example 8. These data show that EN10 mAb antibody inhibits the invasion activity of CL1-5 in a dose-dependent manner.
Figure 8B:
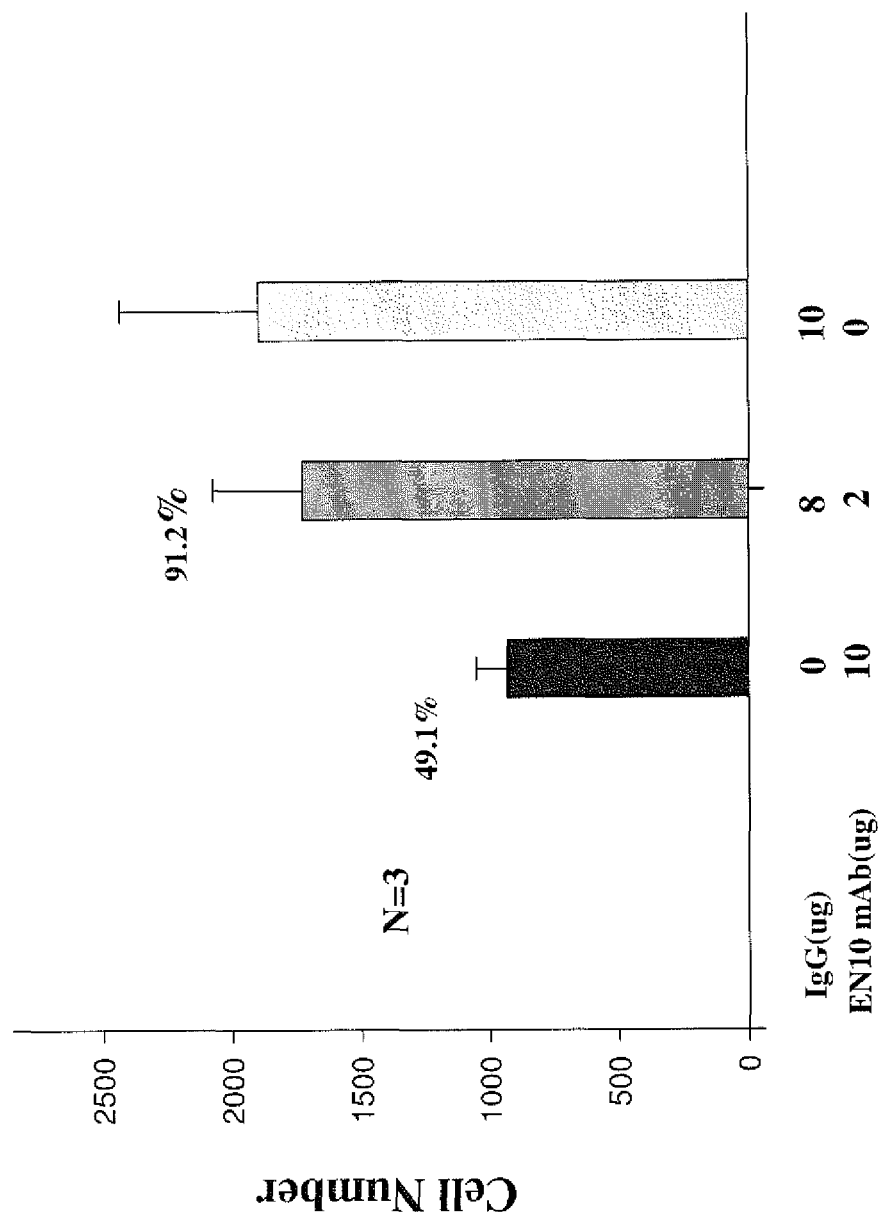
FIG. 8B shows results of invasion activities of U937 cells treated with different concentrations of EN10 mAb isolated from hybridoma, after the surface ENO1 expression of cells was induced by LPS. Detailed procedures were performed as described in Example 8. These data show that the EN10 mAb inhibits the invasion activity of U937 cells in a dose-dependent manner.

The results are shown in the FIGS. 8A and 8B. The invasion activity of CL1-5 was inhibited to an extent ranging from 31±2 to 77±1% (N=3) of the control IgG, when cells were administrated with EN10 mAb from 10 microgram/ml to 100 microgram/ml (FIG. 8A). These results are similar to those of Example 4 and the inhibition is proportional to the concentrations of EN10 mAb with an $EC_{50}$ estimated to be about 30 microgram/ml.

To investigate whether the inhibition of invasion is applicable to the other cancer cells, U937 cells were treated with EN10 mAb ranging from 5 microgram/ml to 50 microgram/ml in a similar manner. The invasion activity of U937 was inhibited to an extent ranging from 91.2±2 to 49.1±1% (N=3) of the control IgG (FIG. 8B). These results indicate that invasion activities of CL1-5 and U937 are inhibited by EN10 mAb in a dose-dependent manner, presumably by inhibiting the plasminogen receptor activity of ENO1.

Example 9

EN10 mAb Recognizes LSP-Induced Surface ENO1 in Lymphoma Cells

A human lymphoma U937 cell line was grown in RPMI containing 10% FCS. Cells were treated with 1 microgram/ml of LPS for 6 hours to induce ENO1 protein expression on the cell surface. For flow cytometric analysis, the intact whole cells were stained with or without EN10 mAb (1:300 dilution), visualized with FITC-conjugated goat anti mouse IgG (Jackson Lab), and analyzed with FACScan flow cytometer (Becton Dickinson). ENO1 expression is measured by the resulting fluorescence intensity.

Figure 9:
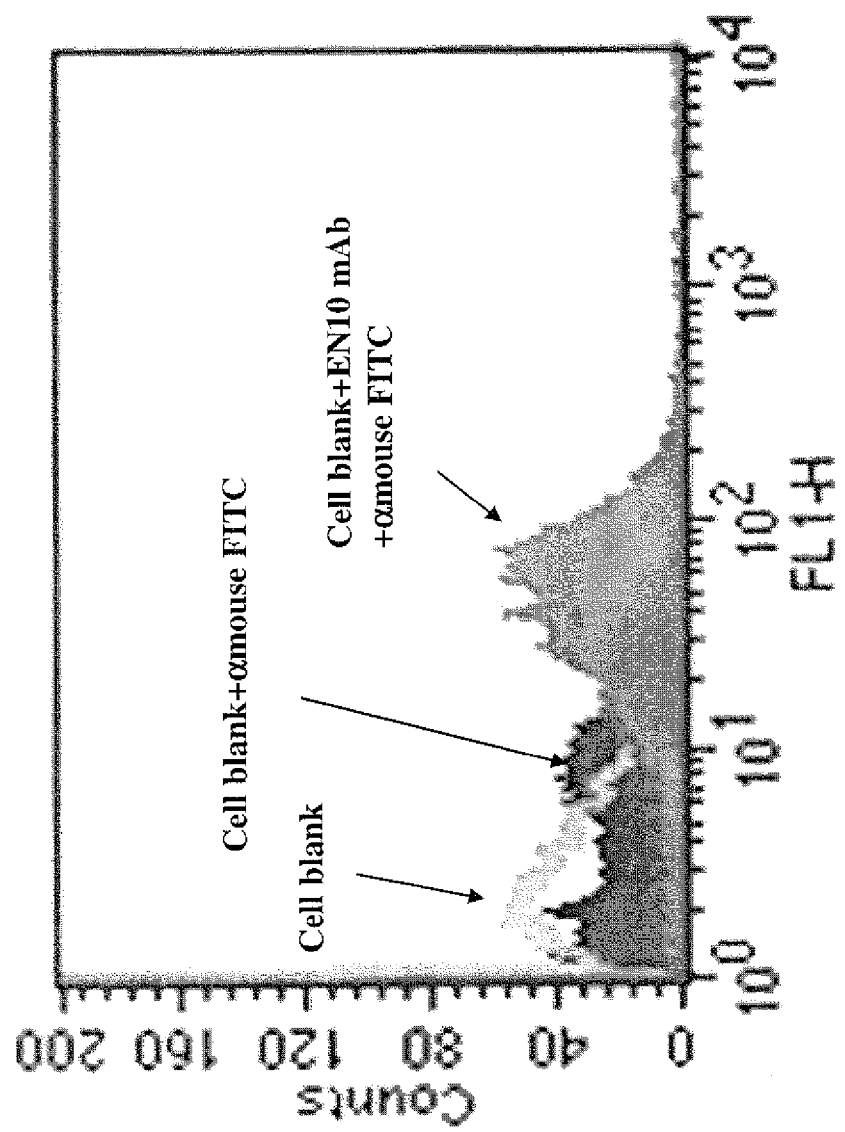
FIG. 9 shows that EN10 mAb recognizes the cell surface ENO1 on U937 cells treated with LPS. Detailed procedures were performed as described in Example 9.

Results from these experiments are shown in FIG. 9. Incubating U937 with LPS and treatment with EN10 mAb shifts the histogram to the right, as compared to incubating the cells without LPS treatment but with EN10 mAb treatment, indicating that U937 cells express ENO1 on their cell surfaces. These data support that EN10 mAb recognizes the LSP-Induced surface ENO1 on lymphoma cells Example 10

EN10 mAb Inhibits the Dissociation of CL-5 Cells from Collagen and Fibronectin

To assess the signal transduction pathway between ENO1 plasminogen receptor-plasmin and extracellular substrates, 1 mg/ml of gelatin, 100 microgram/ml of fibrinogen, 10 microgram/ml of collagen and 10 microgram/ml of fibronectin, respectively, were coated on a non-treated ELISA plate overnight. CL1-5 cells ($4\times10^4$ cells) were seeded on the plate, and 50 microgram/ml of EN10 mAb was added to 200 μL of DMEM containing 10% FCS. Cells were incubated at 37° C. for 24 hours and then washed with PBS twice. 10% WST was added and reaction mixtures were incubated at 37° C. for 4 hours. The relative cell numbers in the plate were estimated by the reading of OD450. Each study was repeated three times. Data are presented as mean±SD. T-test was used to compare activity between each group. P values <0.05 are considered statistically significant.

Figure 10A:
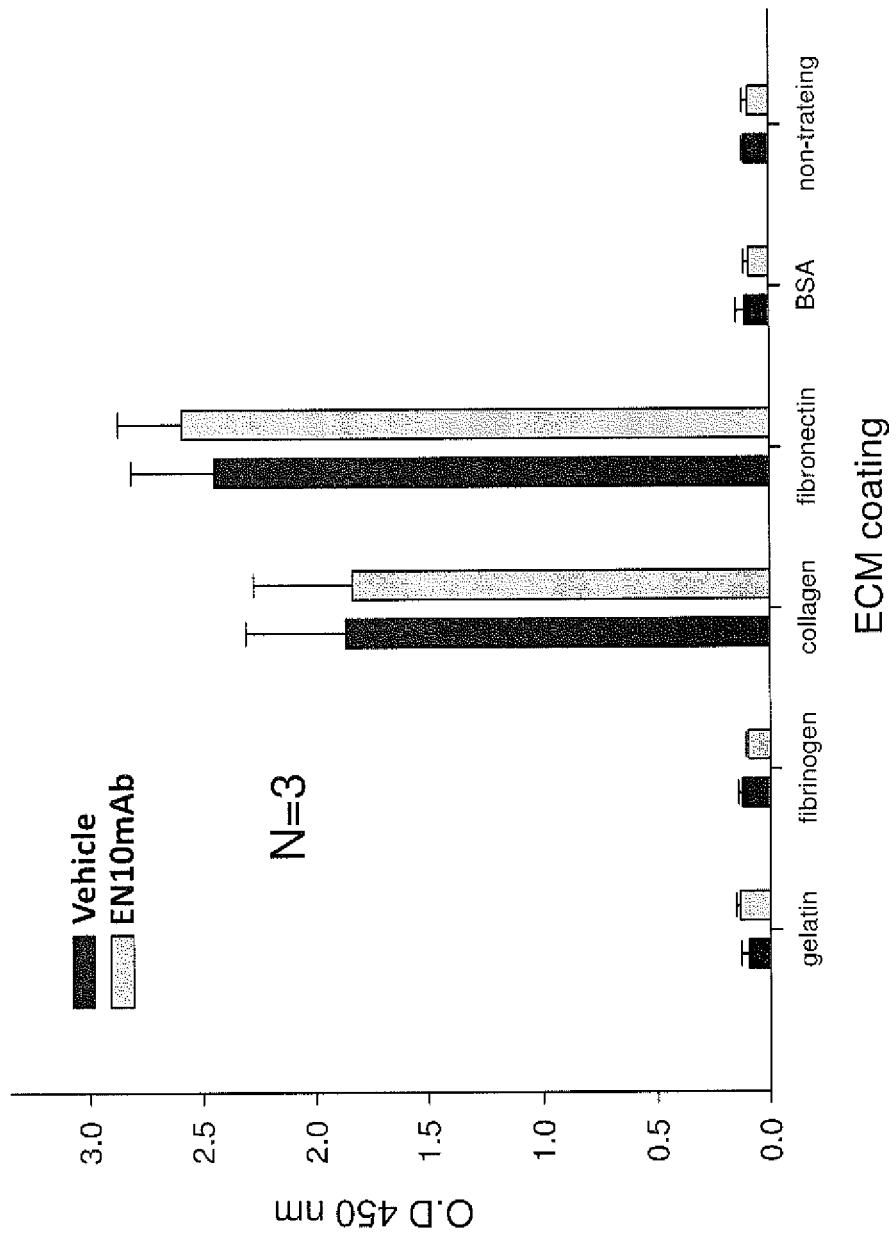
FIG. 10A shows the adhesion activity of CL1-5 lung carcinoma cells to matrix proteins. The adhesion assay was performed as described in Example 10. These data show that CL1-5 cells have higher adhesion activities to collagen and fibronectin.

Results from these experiments are shown in FIG. 10A. These data indicate that OD450 readings on fibronectin and collagen coated plates are 2.45±0.37 (N=3) and 1.83±0.44 (N=3). The readings are much higher than those of gelatin and fibrinogen plates, which are not significant different from the background reading. There are no significant difference between the EN10 mAb treated group and the non-treated group. These results suggest that CL1-5 cells favor binding to fibronectin and collagen, and EN10 mAb is not involved in the cell association pathway when cells are incubated in the medium without down-stream proteases, for example plasminogen and tPA. Data in FIG. 10A suggest that the ENO1 plasminogen receptor activity is not involved in the cell association pathway in the extracellular matrix.

We further tested whether ENO1 takes part in the cell dissociation pathway in the extracellular matrix. One microgram/ml of fibronectin and 10 microgram/ml of collagen were, respectively, coated on a non-treated ELISA plate overnight. CL1-5 cells ($4\times10^4$ cells) were seeded on the plate, and 0, 6.25, 12.5, 25, and 50 microgram/ml of EN10 mAb, respectively, were added to 200 micro L of DMEM containing 10% FCS. Furthermore, 10 microgram/mL Glu-plasminogen and 2 nM tPA were added. Cells were incubated at 37° C. for 24 hours and washed with PBS twice. Then, 10% WST was added and reaction mixtures were incubated at 37° C. for 4 hours. The relative cell numbers in the plate were estimated by the readings of OD450. Each study was repeated three times. Data are presented as mean±SD. T-test was used to compare activity between each group. P values <0.05 are considered statistically significant.

Figure 10B:
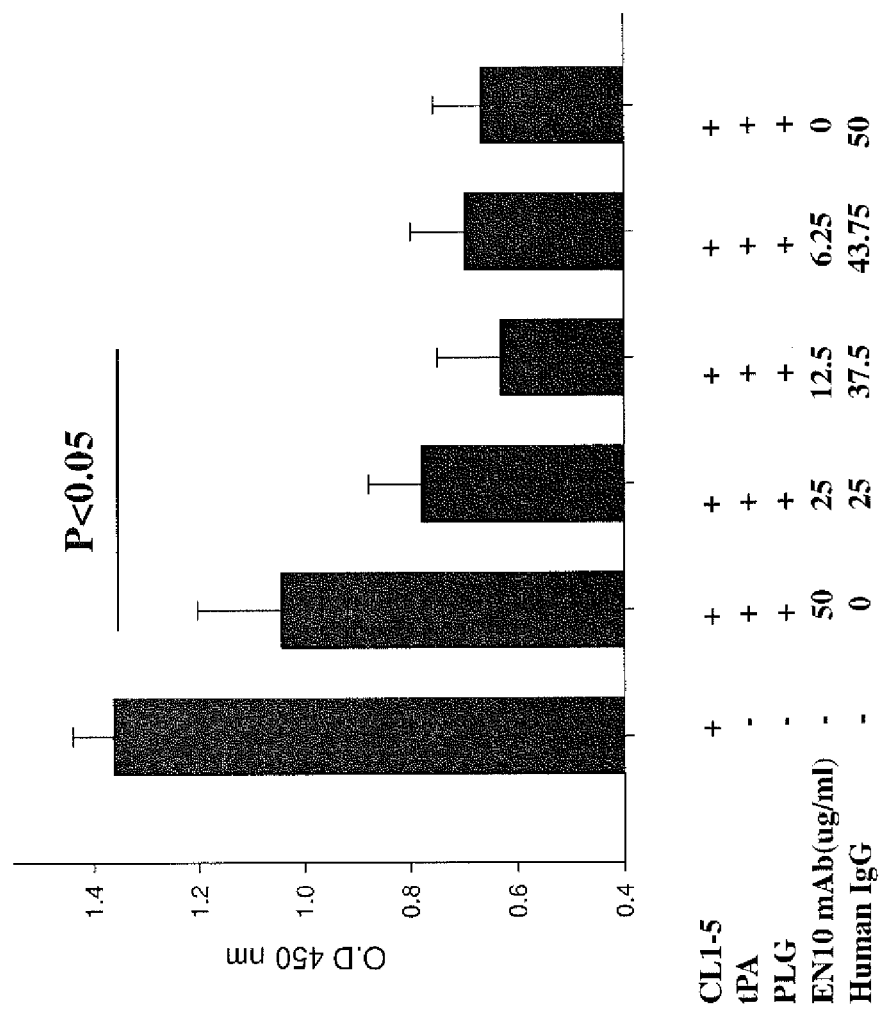
FIG. 10B shows results of inhibition of CL1-5 cell dissociation from fibronectin treated with the EN10 mAb. The cell associated adhesion assay was performed as described in Example 10. These data show that the EN10 mAb inhibits the cell dissociation activity of CL1-5 from fibronectin in a dose-dependent manner.

Results from these experiments are shown in FIG. 10B and FIG. 10C. The data indicate that cell numbers are directly proportional to the concentrations of treated EN10 mAb in both extracellular matrices when the medium contains the ENO1 receptor down-stream proteases plasminogen and tPA. There are significant difference between 50 microgram EN10 mAb treated group and the control IgG group (P<0.05) in both extracellular matrix studies. These results suggest that ENO1 is involved in the dissociation pathway of CL1-5 cells from extracellular matrixes, presumably by enhancing the plasmin and tPA protease activity. EN10 mAb, functioning as an antagonist of ENO1, blocks the receptor activity of ENO1, resulting in the inhibition of plasmin and tPA activation and, therefore, inhibits the dissociation activity of CL1-5 cells from extracellular matrixes and invasion.

Example 11

Preparation of Genes Encoding Monoclonal Antibodies

Cloning of the gene encoding the antibody EN10 mAb is performed in accordance with the methods described below.

(1) cDNA Cloning of Antibody Genes and Preparation

The hybridoma was cultured in a RPMI medium (manufactured by Gibco) containing 10% FCS. After the cell number reached about $10\times10^6$/ml, the cells were collected by centrifugation, and then TRIzol® (manufactured by Invitrogen) was added to extract total RNA in accordance the instruction manual. Cloning the variable region of the antibody cDNAs was performed using a mouse Ig-primer set (manufactured by Novagen) in accordance with the attached instruction manual.

(a) The synthesis of 1st Strand cDNA was performed in accordance with the instruction manual of SuperScript® III First-Strand Synthesis System (manufactured by Invitrogen).

The 1st strand cDNA was prepared using 5 microgram of the total RNA as a template. Five microgram of total hybridoma RNA, 1. microL of 50 ng/microL of random primers, and 1 microL of 10 mM dNTP were mixed, and DEPC-treated water was added to 10 microL in a 2001 PCR tube. The reaction mixture was incubated at 65° C. for 5 min, and then placed on ice for at least 1 minute. Ten (10) microL of cDNA Synthesis Mixture containing 2 microL of 10×RT buffer, 4 microL of 25 mM $MgCl_2$, 2 microL of DTT, 1 microL of 4 unit RNaseOUT™, and 1 microL of 200 unit SuperScript® III RT were added, mixed gently, and collected by brief centrifugation. The reaction tube was incubated for 10 min at 25° C. and followed by 50 min at 50° C. The reaction was terminated at 85° C. for 5 min and chilled on ice. The tube was briefly centrifuged to collect the reaction, and 1 microL of RNase H was added and incubated for 20 min at 37° C.

(b) Amplification by PCR of heavy chain genes and light Chain genes

A reaction solution having a composition of 5 microL of cDNA, 5 microL of 10× reaction Buffer, 1 microL of 10 mM dNTP mix, 1 microL of 2.5 unit Taq polymerase, and 1 microL of forward primer 1 and 1 microL of reverse primer 2 provided by the primer set was prepared in a final volume of 50 microL with double distilled water and subjected to PCR.

For amplification of the light chain and heavy chain of an antibody, a cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. The reaction solution was subjected to 2% agarose gel electrophoresis to analyze the reaction products. Products with the correct molecular weights, about 463 bps for the heavy chain and 451 bps for the light chain, were ligated to a pCR 2.1-TOPO vector (manufactured by Invitrogen) for subcloning in accordance with the attached instruction manual. M13 forward (5'-GTAAACAAC GACGGC-GAG-3'(SEQ ID NO:11) and M13 reverse (5'-CAG GAA ACA GCT ATG AC-3' (SEQ ID NO:12)) primers were then used to determine the nucleotide sequence. Based on the sequence information, antibody sequences were translated into proteins sequences by ExPASY-Translation Tool. Resulting sequences of EN10 mAb comprise a heavy chain amino acid sequence and a light chain sequence having complementarity determining regions (CDR), which were determined by the method published by Kabat et al., Sequences of Proteins of Immunological Interest, Fifth Edition, NIH Publication 91-3242, Bethesda Md. (1991), vols. 1-3.

FIG. 11A depicts the variable heavy chain region amino acid sequence of EN10 mAb (SEQ ID NO: 1). The framework regions (FR1, FR2, FR3, and FR4) and CDRs (HCDR1 (SEQ ID NO: 3), HCDR2 (SEQ ID NO: 4), and HCDR3 (SEQ ID NO: 5) are indicated.

FIG. 11B depicts the variable light chain region amino acid sequences of EN10 mAb (SEQ ID NO: 2). The framework regions (FR1, FR2, FR3, and FR4) and CDRs (LCDR1 (SEQ ID NO: 6), LCDR2 (SEQ ID NO: 7), and LCDR3 (SEQ ID NO: 8) are indicated.

Example 12

Epitope Mapping

Antibody Epitope Mapping

To determine the epitope of EN10 Mab on the human ENO1 protein, two forward primers, with the nucleotide sequences of 5'-GGATCCGCAGCAAACTTCAGG-GAAGCCATG-3'(SEQ ID NO:13), and 5'-GGATCCTC-GAAGATCCCTTTGACCAGGATG-3' (SEQ ID NO:14), and a reverse primer (5'-TCAGGCTGAAAATCTCTCATC-CGC-3 (SEQ ID NO:15) were designed. An *E. coli* expression plasmid pTRC-HIS ENO1 containing human ENO1 cDNA gene was used as a template to amplify ENO1 deletion mutants. Primers with SEQ NO:13 and SEQ NO:14 were used as forward primers, with the SEQ ID NO:15 as a reverse primer, to amplify deletion mutants Δ1-189 (FIG. 12A) and Δ1-297 (FIG. 12A), respectively. The other set of primers, having the sequences of 5'-GGATCCTATCTATTCTCAA-GATCCATGCC-3' (SEQ ID NO:16) and 5'-CTCGAGGT-CATGGTGTCTCATCGTTCGCTCGAG-3' (SEQ ID NO:17), was used to amplify a deletion Δ297-434 mutant. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of the forward primer, and 1 microL of the reverse primer was prepared in a final volume of 50 microL with double distilled water and subjected to PCR. A cycle of 94 degree C. for 10 minutes was used, then a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1-TOPO vector (manufactured by Invitrogen) for subcloning in accordance with the attached instruction manual. M13 forward (5'-GTAAACAACGACGGCGAG-3'(SEQ ID NO: 11) and M13 reverse (5'-CAG GAAACA GCT ATG AC-3' (SEQ ID NO: 12)) primers were then used to determine the nucleotide sequence. Every mutation clone with the correct sequences was digested with restriction enzymes BamHI and XhoI, and the digestion products were subjected to 2% agarose gel electrophoresis. The insertion fragment of each mutant was cut from the agarose gel and purified with a Gene Clean Kit in accordance with the attached instruction manual provided by the manufacturer (BIO101). The BamHI and XhoI DNA fragment of each mutant was ligated to the BamHI and XhoI sites of an *E. coli* expression vector pTRC His A (Invitrogen). The resulting plasmid was transformed into *E. coli* BL21 Rosseta. The ENO1 mutation protein was expressed in *E. coli* by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of human ENO1 protein was coated on a 96-well ELISA plate and plate was washed by PBS. 10 microgram of EN10 mAb was added to the plate and the plate was incubated at 37° C. for 1 hours. After the binding complex was washed with PBS twice, a goat anti-mouse IgG conjugated with HPRT was added. After 1 hour incubation, TMB was added. The binding affinity was determined by the readings of OD 405. Each study was repeated three times. Data are presented as mean±SD. T-test was used to compare activity between each group. P values <0.05 were considered statistically significant.

Figure 12A:
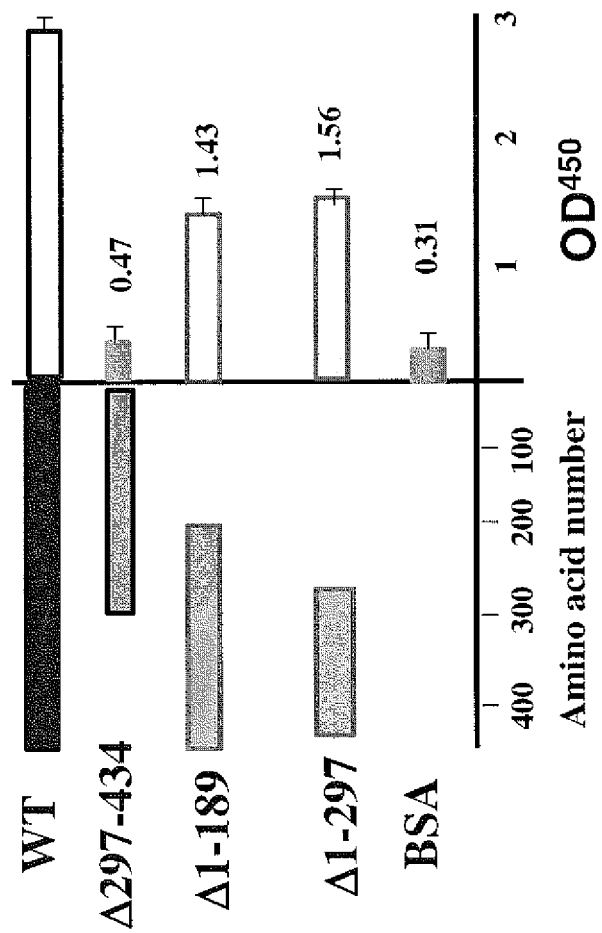
FIG. 12A shows the EN10 mAb binding activities of deletion mutants of ENO1. The binding epitope of EN10 mAb is located between the amino residue number 293 and 434 of human ENO1 protein. The large portion deletion of ENO1 to determine the binding region of EN10 mAb was performed as described in Example 12.

The results are shown in FIG. 12A. ENO1 mutants Δ1-189 and Δ1-297 have OD405 readings about 1.43±0.18 and 1.56±0.08 (N=3) (these are 1.43 and 1.56 in FIG. 12A), which are about 42% and 39% of that of the wild type ENO1 (2.87±0.08) (N=3), respectively. However, when amino acid residues from 297 to 434 were deleted, the binding activity of this mutated ENO1 to EN10 mAb was lost, as compared with the BSA background. These results suggest that amino acid residues from 297 to 434 are required for ENO1 protein binding to EN10 mAb and the decrease in the binding activity of mutants Δ1-182 and Δ1-297 may be due to the instability or conformation change of the mutant proteins.

To further explore the epitope of EN10 mAb in the ENO1 protein, 5 reverse primers, having sequences of 5'-CTC-GAGAGGGATCTTCGATAGACACCACTGGG-3' (SEQ ID NO:18), 5'-CTCGAGCTACCTGGATTCCTGCACTG-GCTG-3' (SEQ ID NO:19), 5'-CTCGAGACTTCTCGT-TCACGGCCTTGGCGATC-3' (SEQ ID NO:20), 5% CTC-GAGACTTCTCGTTCACGGCCTTGGCGATCC-3' (SEQ ID NO:21), 5'-CTCGAGCAGTCTCCCCCGAACGAT-GAGA CACC-3' (SEQ ID NO:22), and 5'-CTCGAG CAC-CAGTCTTGCCCAGTGCAC-3'(SEQ ID NO:23) were designed. An E. coli expression plasmid pTRC-HIS ENO1 containing human ENO1 cDNA gene was used as a template to amplify the ENO1 deletion mutants. SEQ ID NO:16 were used as the forward primer to amplify deletion mutants 296-434, 316-434, 336-434, 376-434 and 396-434 with the SEQ ID NO:18, SEQ ID:19, SEQ ID:20, SEQ ID:21, SEQ ID:22, and SEQ ID:23 primers, respectively. For amplification of each mutant, a reaction solution having a composition of 1 microL of 1:1000 dilution of template DNA about 0.1 ng, 5 microL of 10× reaction buffer, 1 microL of 10 mM dNTP mix, 1 microL of 2.5 unit Taq polymerase, 1 microL of forward primer, and 1 microL of reverse primer was prepared in a final volume of 50 microL with double distilled water and subjected to PCR. A cycle of 94 degree C. for 10 minutes was used. Then, a cycle of 94 degree C. for one minute, 52 degree C. for one minute, and 72 degree C. for 1 minute was repeated 35 times, and the reaction was incubated at 72 degree C. for 10 more minutes. This reaction solution was subjected to 2% agarose gel electrophoresis to analyze the reaction products. Reaction products with the correct molecular weights were ligated into a pCR 2.1-TOPO vector (manufactured by Invitrogen) for subcloning in accordance with the attached instruction manual. M13 forward (5'-GTAAACAACGACG-GCGAG-3' (SEQ ID NO:11) and M13 reverse (5'-CAGGAA ACAGCTATGAC-3' (SEQ ID NO:12) primers were then used to determine the nucleotide sequence. Every mutation clone with the correct sequence was digested with restriction enzymes BamHI and XhoI and the digestion product was subjected to 2% agarose gel electrophoresis. The DNA fragment of each mutant was isolated from the agarose gel and purified with a Gene Clean Kit in accordance with the attached instruction manual provided by the manufacturer (BIO101). The BamHI and XhoI DNA fragment of each mutant was ligated into the BamHI and XhoI sites of an E. coli expression vector pTRC His A (Invitrogen). The resulting plasmid was transformed into E. coli BL21 Rosseta. The ENO1 mutation protein was expressed in E. coli by IPTG induction and purified by Ni-agarose in accordance with the attached instruction manual provided by the manufacturer (Qiagen) after the bacteria pellet was sonicated. The purity of each mutant was analyzed by 12% SDS PAGE. To determine the binding activity of each mutant protein, 400 ng of human ENO1 protein or mutant protein was coated on a 96-well ELISA plate and plate was washed by PBS. 10 microgram of EN10 mAb was added and incubated at 37° C. for 1 hours. After the binding complex was washed with PBS twice, a goat anti-mouse IgG conjugated with HPRT was added. After 1 hour incubation, TMB was added. The binding affinity was determined by the readings of OD 405. Each study was repeated three times. Data are presented as mean±SD. T-test was used to compare activity between each group. P values <0.05 are considered statistically significant.

Figure 12B:
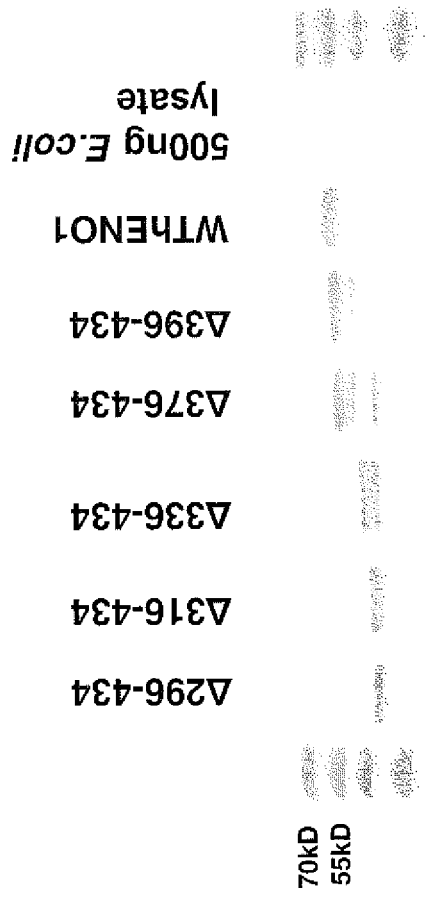
FIG. 12B shows the 12% SDS PAGE of 6 C-terminal deletion mutant protein of ENO1 purified from E. coli. The detailed procedures for the purification of ENO1 deletion mutants are described in Example 12.
Figure 12C:
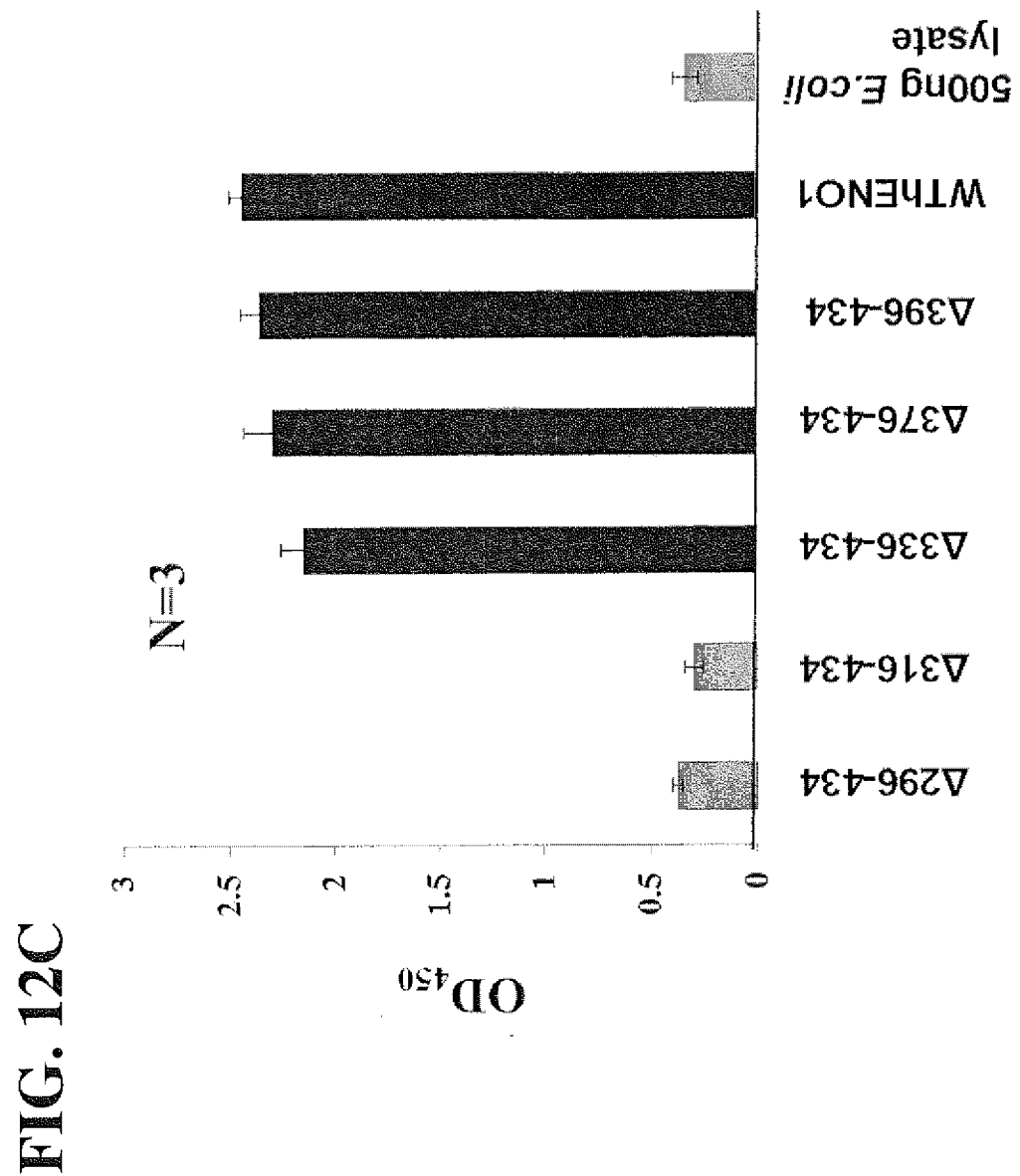
FIG. 12C shows the EN10 mAb binding activities of 6 C-terminal deletion mutants of ENO1. The binding epitope of EN10 mAb is located between amino residue number 296 and 336 of human ENO1 protein. The large portion deletion of ENO1 to determine the binding region of EN10 mAb was performed as described in Example 12.

The 12% of SDS PAGE of each mutant and the wild type protein are shown in the FIG. 12B. The molecular weight of each mutant increases from the mutant 296-343 to the wild type. This result suggests that we can yield the whole protein from each mutant even though some degradation of mutants 336-434 and 376-434 can be seen. As showed in the FIG. 12C, there is no significant difference between the EN10 mAb binding affinity of the wild type ENO1 and those of deletion mutants 336-434, 376-434, and 369-343. However, when amino acid residues from 296 to 316 and 317 to 336 are deleted, the EN10 mAb binding activities of these two ENO1 mutants are lost, as compared with that the E. coli cell lysate background. These results suggest that amino acid residues from 296 to 336 (FDQDDWGAWQKFTASAGIQVVGD-DLTVTNPKRIAKAVNEKS, SEQ ID NO. 49) are important for ENO1 protein binding with EN10 mAb.

Example 13

Alanine Scanning

To further explore which residues from 296 to 336 of human ENO1 are important for EN10 mAb binding, the crystal structure of ENO1 was downloaded from protein data bank (pdb-entry: 2PSN). After the structure analysis, amino acid residues D300, W301, G302, Q305, K306, A309, K326, K330, N333, E334, and K335 are predicted to be exposed on the protein surface and are candidates for mutations to analyze whether they are indeed important for EN10 mAb binding. 10 of these 11 residues were chosen to be mutated to alanine, except for A309 which was mutated to glycine using the QuickChange II site-directed mutagenesis Kit in accordance with the attached instruction manual provided by the manufacturer (Agilent Technology). The following mutagenic oligonucleotides for alanine scanning (Table 1) were generated by Genomics BioScience and Technology Co., Ltd.

TABLE 1

Oligo Sequences (SEQ ID NO: 24)
5'-GATCCCTTTGACCAGGATGCCTGGGGAGCTTCGCAG-3'

(SEQ ID NO: 25)
5'-CTGCCAAGCTCCCCAGGCATCCTGGTCAAAGGGATC-3'

(SEQ ID NO: 26)
5'-CCCTTTGACCAGGATGACGCCGGAGCTTGGCAGAAG-3'

(SEQ ID NO: 27)
5'-CTTCTGCCAAGCTCCCGCGTCATCCTGGTCAAAGGG-3'

(SEQ ID NO: 28)
5'-CTTTGACCAGGATGACTCGCCAGCTTGGCAGAAGTTC-3'

(SEQ ID NO: 29)
5'-GAACTTCTGCCAAGCTGCCCAGTCATCCTGGTCAAAG-3'

TABLE 1-continued

Oligo Sequences (SEQ ID NO: 30)
5'-GACTGGGGAGCTTGGGCGAAGTTCACAGCCAGTGCA-3'

(SEQ ID NO: 31)
5'-TGCACTGGCTGTGAACTTCGCCCAAGCTCCCCACTC-3'

(SEQ ID NO: 32)
5'-GGGGAGCTTGGCAGGCGTTCACAGCCAGTGCAGG-3'

(SEQ ID NO: 33)
5'-CCTGCACTGGCTGTGAACGCCTGCCAAGCTCCCC-3'

(SEQ ID NO: 34)
5'-GGCAGAAGTTCACAGGCAGTGCAGGAATCCAGGTAG-3'

(SEQ ID NO: 35)
5'-CTACCTGGATTCCTGCACTGCCTGTGAACTTCTGCC-3'

(SEQ ID NO: 36)
C5'-TCACAGTGACCAACCCAGCGAGGATCGCCAAGGCC-3'

(SEQ ID NO: 37)
5'-GCCTTGGCGATCCTCGCTGGGTTGGTCACTGTGAG-3'

(SEQ ID NO: 38)
5'-CAACCCAAAGAGGATCGCCGCGGCCGTGAACGAGAAG-3'

(SEQ ID NO: 39)
5'-CTTCTCGTTCACGGCCGCGGCGATCCTCTTTGGGTTG-3'

(SEQ ID NO: 40)
5'-GAGGATCGCCAAGGCCGTGGCCGAGAAGTCCTGCAAC-3'

(SEQ ID NO: 41)
5'-GTTGCAGGACTTCTCGGCCACGGCCTTGGCGATCCTC-3'

(SEQ ID NO: 42)
5'-GATCGCCAAGGCCGTGAACGCGAAGTCCTGCAACTG-3' C (SEQ ID NO: 43)
5'-GCAGTTGCAGGACTTCGCGTTCACGGCCTTGGCGATC-3'

(SEQ ID NO: 44)
5'-GCCAAGGCCGTGAACGAGGCGTCCTGCAACTGCCTC-3'

(SEQ ID NO: 45)
5'-GAGGCAGTTGCAGGACGCCTCGTTCACGGCCTTGGC-3'

(SEQ ID NO: 46)
5'-CAAGGCCGTGAACGCGGCGTCCTGCAACTGCCTCCTG-3'

(SEQ ID NO: 47)
5'-CAGGAGGCAGTTGCAGGACGCCGCGTTCACGGCCTTG-3'

For amplification of each mutant, a reaction solution having a composition of 3 microL of template DNA about 30 ng, 5 microL of 10× reaction buffer, 1 microL of 10 mM dNTP mix, 1 microL of 2.5 unit pfu polymerase, 12.5 microL of 125 ng forward primer, and 12.5 microL of 125 ng reverse primer was prepared in a final volume of 50 microL with double distilled water and subjected to PCR. A cycle of 95 degree C. for 10 minutes was used. Then, a cycle of 95 degree C. for 30 seconds, 55 degree C. for 30 seconds, and 68 degree C. for 6 minute was repeated 16 times. After the PCR reaction, 1 microL of DpnI was added to each PCR tubes, incubated at 37° C. for 1 hour and then DpnI was heated to be inactivated at 80° C. for 20 minutes. The reaction products were transformed to 50 microL XL1-Blue competent cells in accordance with the attached instruction manual (manufactured by Invitrogen). An ENO1 R400-420 primer (5'-GCAAGGGGCACCAGTCTTGATCTG-3' (SEQ ID NO:48)) was used to determine the nucleotide sequence.

Every mutation clone plasmids with correct sequences were transformed to *E. coli* BL21 Rosseta. The ENO1 mutation protein was expressed in *E. coli* by IPTG induction and purified by Ni-agarose in accordance with the attached instruction manual provided by the manufacturer (Qiagen) after the bacteria pellet was sonicated. The purity of each mutant protein was analyzed by 12% SDS PAGE.

To determine the binding activity of each mutant protein, 400 ng/100 microL of human ENO1 protein or mutated ENO1 protein was coated on a 96-well ELISA plate overnight at 4° C. and the plate was washed with PBS. The plate was blocked with 1% BSA (w/v) in PBS at room temperature for 1 hour, then washed again with 1×PBS. A primary antibody (EN10 mAb) was 2-fold serial diluted to 15 different concentrations and added to the plate at 37° C. for 1 hour. After the reaction was done, the plate was washed 3 times with 1×PBS. A 1/8000 dilution of goat anti-mouse-HRP antibody was added and incubated at 37° C. for 1 hour, then the plate washed 3 times with 1×PBS. Then, TMB substrate was added and the reaction was allowed to proceed at room temperature for 30 minutes. The reaction was stopped by adding 1N HCl and OD 450 was read to determine the activity. Each study was repeated three times. Data are presented as mean±SD. OD readings and concentrations of antibody were used to make a multiple scatter plot using Sigmaplot™. The $K_d$ values were predicted by four parameter logistic fit.

According to the ENO1 large portion deletion study results shown in Example 9, a peptide sequence FDQDDW-GAWQKFTASAGIQVVGDDLTVTNPKRIAKAVNEKS (SEQ ID NO:49) from the residue number 296 to 336 is required for tight binding of ENO1 protein with EN10 mAb. "Tight binding" as used herein refers to binding between a specific binding agent (e.g., an antibody, an scFv or Fab fragment) and a ligand/target (e.g., a peptide, protein, or cell) with a dissociation constant ($K_d$) of 10 nM or lower, preferably 1.0 nM or lower.

Figure 13A:
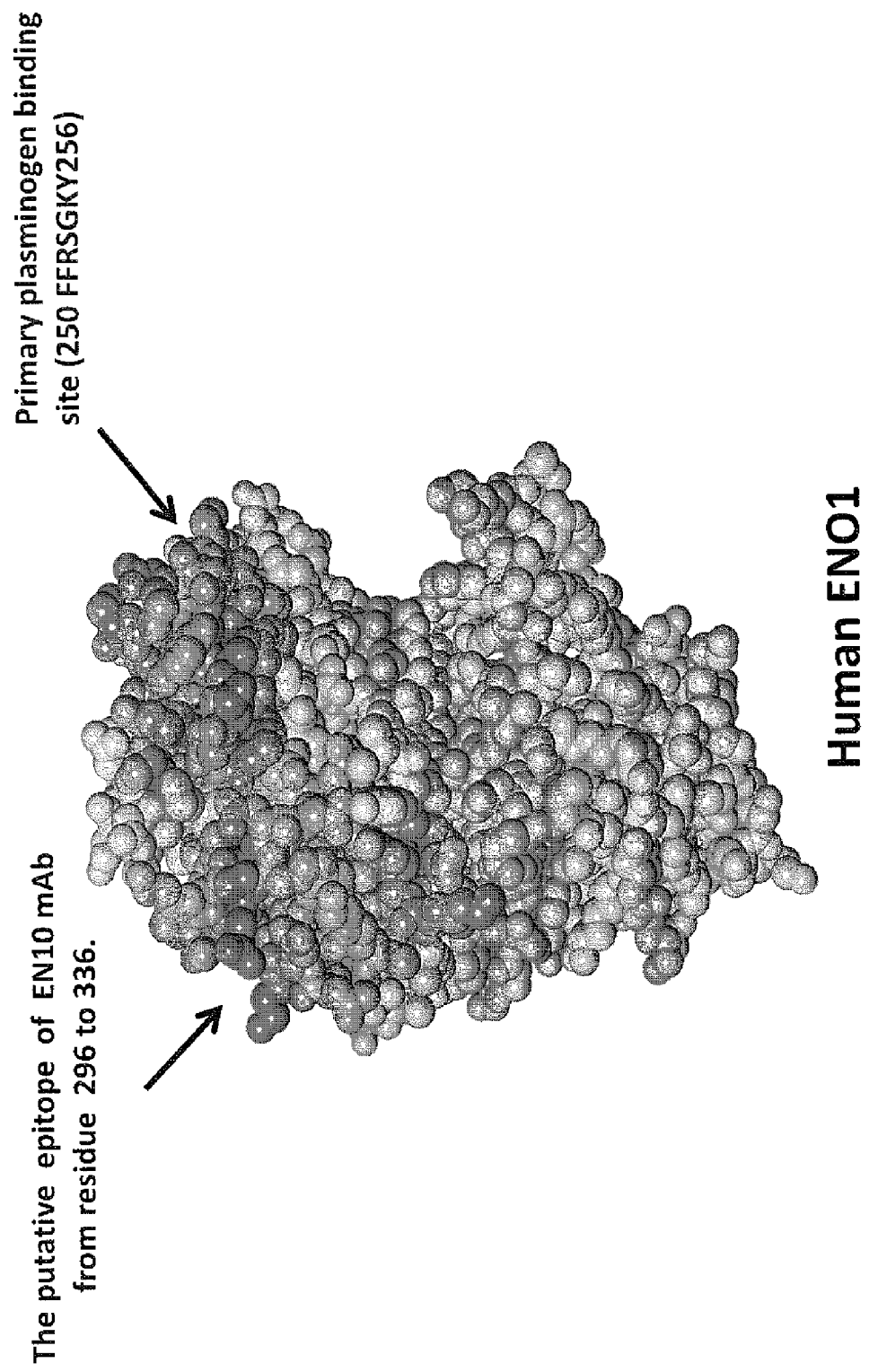
FIG. 13A depicts the crystal structure and surface-expose amino acid residues between amino number 296 and 336 of human ENO1. The structure prediction was described in Example 13.
Figure 13B:
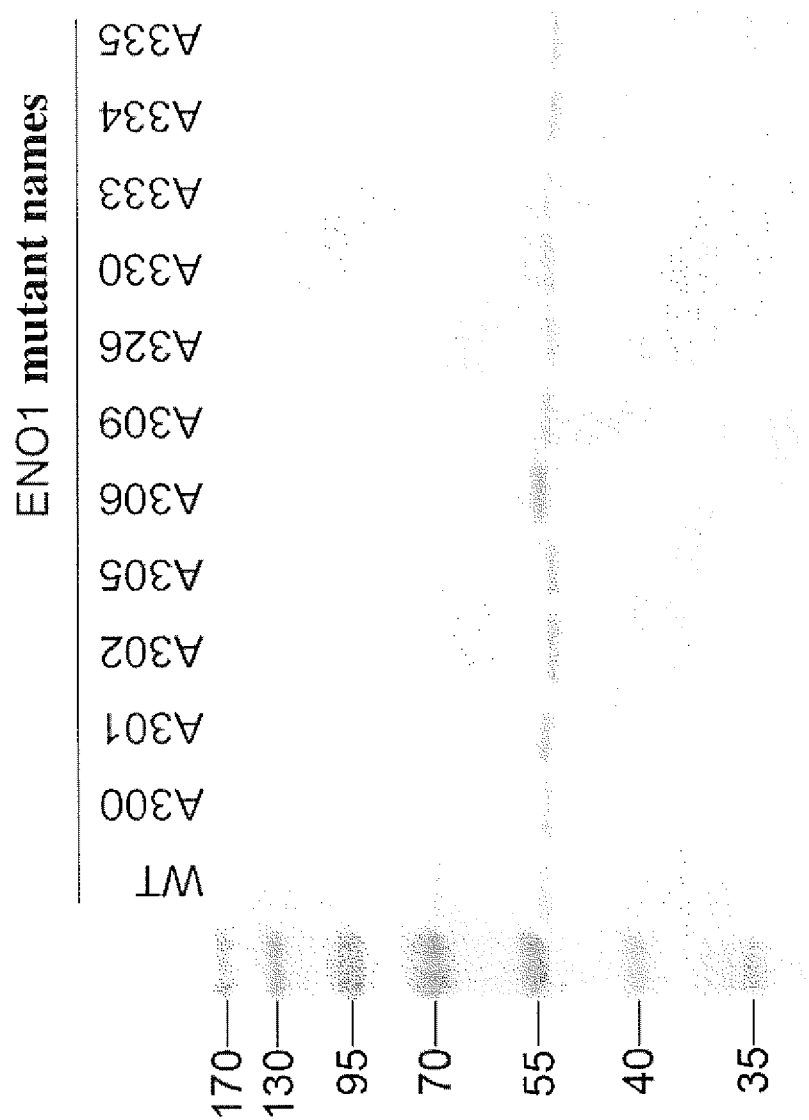
FIG. 13B shows the 12% SDS PAGE of 11 alanine scanning mutant proteins of ENO1 purified from E. coli. The detailed procedures for the purification of ENO1 mutation proteins are described in Example 13.

The above deletion experiments identify residues 296 to 336 on ENO1 as the region for the antibody binding. To further characterize the actual binding sites (e.g., epitopes), the crystal structure of ENO1 was downloaded from protein data bank (pdb-entry: 2PSN) to analyze residue positions from this region. There are eleven amino acid residues including D300, W301, G302, Q305, K306, A309, K326, K330, N333, E334, and K335 exposed on the protein surface (FIG. 13A, putative epitope). By site-direct mutagenesis, these 11 amino acids were mutated and resulting mutant proteins were expressed in *E. coli* and purified, respectively (FIG. 13B). Every purified ENO1 mutant protein was analyzed for any $K_d$ changes (as compared with ENO1 binding) using ELISA.

Figure 13C:
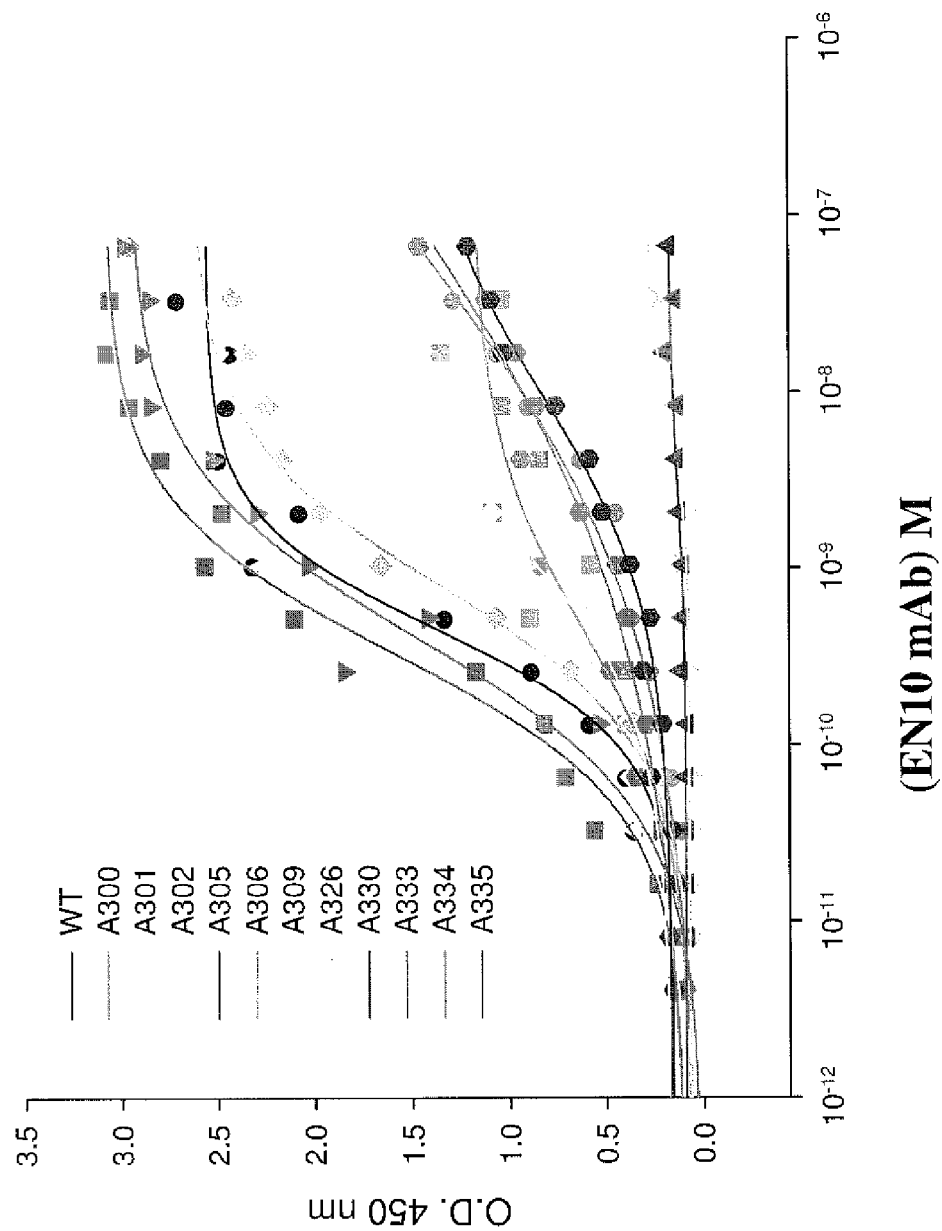
FIG. 13C shows the ENO1 binding ELISA and $K_d$ values of 11 alanine scanning mutants against EN10 mAb. The result suggests that sequences of ENO1 peptide 1, FD Q D D W G A W Q K F TA (SEQ ID NO: 9), and peptide 2, K R I A K A V N EK S (SEQ ID NO:10), located between amino residue number 296 and 336 of human ENO1 are involved in EN10 mAb binding. The alanine scanning was performed as described in Example 13.

The results indicate that there are three functional classes of amino acid residues in these mutants. Amino acid residues W301 and K330 are important for the binding between ENO1 protein and EN10 mAb. If these two amino acid residue are mutated to alanine, respectively, the binding activities of these two ENO1 mutants to EN10 mAb are significantly compromised. The second class of amino acid residues includes A309, E334, K335 and D300. If E334, K335 and D300 are mutated to alanine or the A309 is mutated to glycine, respectively, the binding activities of these ENO1 mutants to EN10 mAb are compromised. The rest of amino acid residues including G302, Q305, K306, N333, and K326 belong to the group of amino acids residues that have no significant binding effects on ENO1 protein binding to EN10 mAb (FIG. 13C and Table 2). These results suggest that W301, K330 A309, E334, K335 and D300 are important for the protein-protein binding between ENO1 and EN10 mAb. These amino acid residues belong to sequences of ENO1 peptide 1, $^{296}$F D Q D D W G A W Q K F T A$^{309}$ (FIG. 13D, SEQ ID NO:9) and peptide 2, $^{326}$K R I A K A V N EK S$^{336}$ (FIG. 13D, SEQ ID NO:10), which may be the binding epitopes of EN10 mAb in the amino residue number from 296 to 335 (FIG. 13D; SEQ ID NO:49) of human ENO1.

TABLE 2

Mutant K$_d$ Values

| Mutant | KD | Mutant | KD | Mutant | KD |
|---|---|---|---|---|---|
| Wild type | $4.43 \pm 0.65 \times 10^{-10}$ | A300 | $6.33 \pm 2.57 \times 10^{-8}$ | A301 | Non-detected |
| A302 | $3.45 \pm 0.28 \times 10^{-10}$ | A305 | $3.31 \pm 0.50 \times 10^{-10}$ | A306 | $4.65 \pm 2.42 \times 10^{-10}$ |
| A309 | $5.63 \pm 2.67 \times 10^{-9}$ | A326 | $7.87 \pm 1.35 \times 10^{-10}$ | A330 | Non-detected |
| A333 | $4.13 \pm 1.09 \times 10^{-10}$ | A334 | $1.07 \pm 4.39 \times 10^{-7}$ | A335 | $9.57 \pm 3.72 \times 10^{-9}$ |

Example 14

Structure Analysis of ENO1 and EN10 mAb

The crystal structure of Enolase alpha was downloaded from protein data bank (pdb-entry: 2PSN). The Fab fragment structure of EN10 mAb was built by the homology modeling. The first step was to find a template structure with high sequence similarity to the EN10 mAb. The NCBI database (www.ncbi.nlm.nih.gov.) was searched and many highly homologous hits were found. The heavy-chain framework (pdb-entry: 3DGG) (identity 89%) and the light chain framework (pdb-entry: 1F6L) (identity 95%) were chosen. The antibody homology model of EN10 mAb was constructed with the programs Accelrys Discovery Studio. ENO1 and antibody structures were used for docking. In order to alleviate the computational load, only the CDR loops of variable domain of the antibodies were docked to ENO1. The framework of antibody was fixed. Since the docking procedure explores a relative large area around the starting position, very careful initial positioning of the docking partners was not required. When using ZDock, the structures were perturbed with x-y-z axis movements (perturbation along the line of centers, in angstroms perturbation in the plane perpendicular to the line of centers, in angstroms-rotational perturbation, in degrees) and approximately 5000 poses were generated for each docking run. Clustering analysis of the ZDock results was conducted with both a 5 Å and 10 Å cut-off. The interaction residues of ENO1 were chosen for epitope mapping.

Figure 14A:
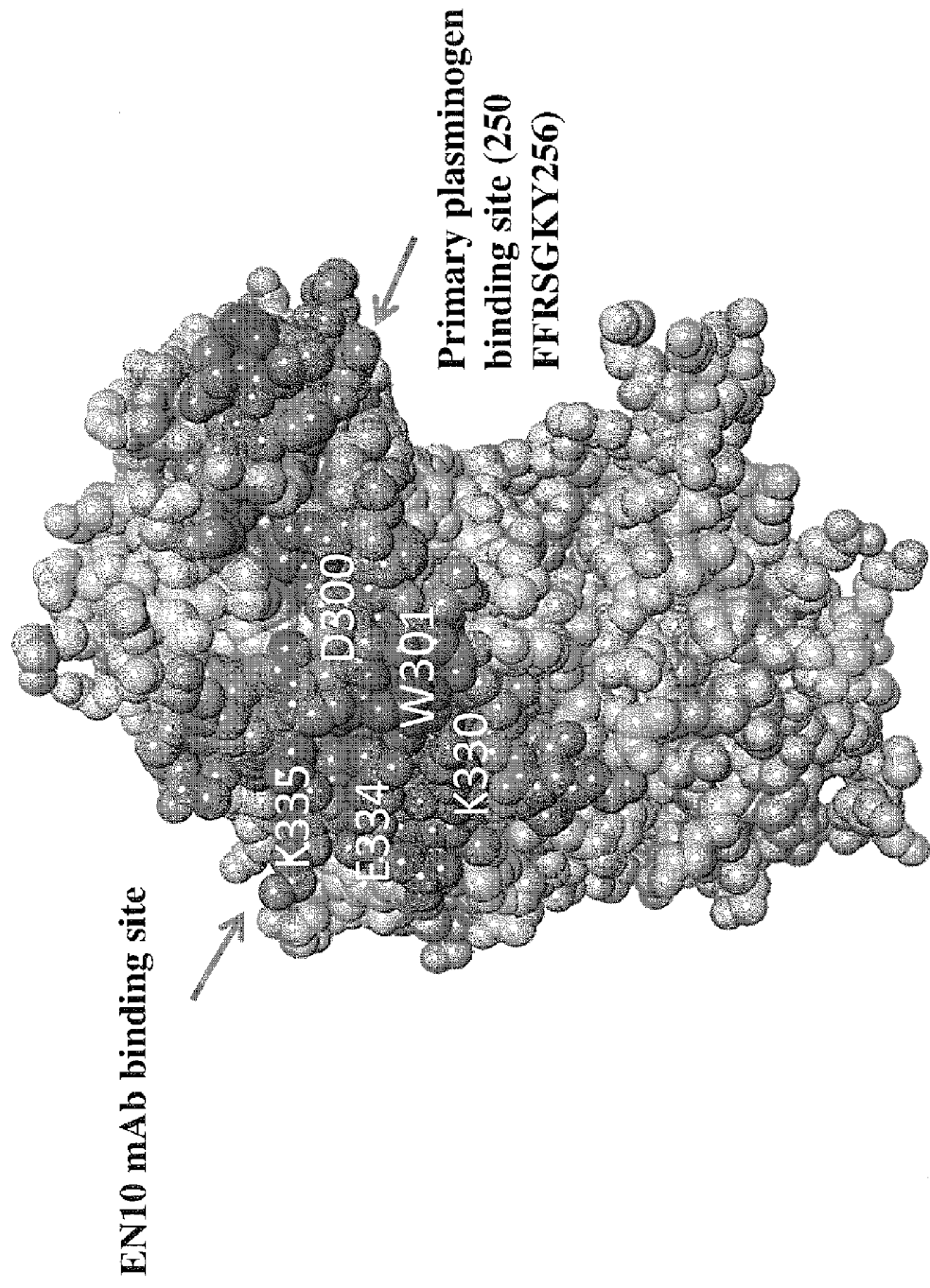
FIG. 14A shows a 3D structure of human ENO1 protein.
Figure 14B:
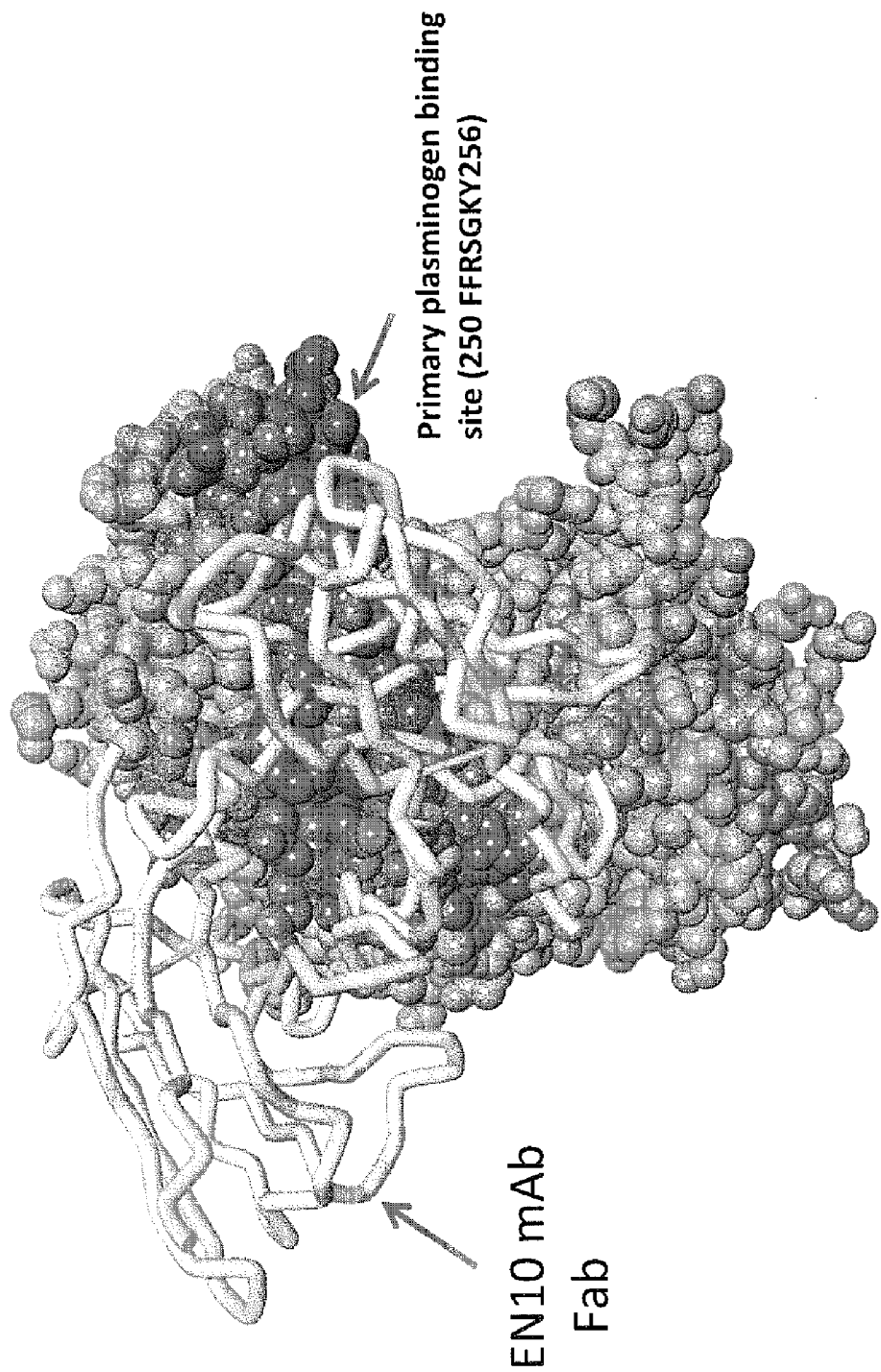
FIG. 14B depicts the deduced structure of EN10 mAb Fab (shown in ribbon-helix, light chain grey, heavy chain black) in complex with the plasminogen binding region of human ENO1 protein. Crystal structure prediction of ENO1 protein and EN10 mAb was performed as described in Example 14.

3D structure of human ENO1 protein is shown in FIG. 14A. Amino acid residues W301, K330, 300D, E334, AND K335 are labeled. The critical residues in plasminogen binding site of ENO1 protein published by Wang et al. are indicated (250-FFRSGKY 256). FIG. 14B shows that the binding complex of ENO1 and EN10 mAb is predicted about 5 Å to 15 Å close to the plasminogen binding site of ENO1. The gap between plasminogen binding site and EN10 mAb is far less than 34 Å, which is the molecular sized of human plasminogen. This study suggests that the binding of ENO1 and EN10 mAb shields the plasminogen binding site of ENO1, prevents the access of plasminogen to ENO1, results in compromising the plasminogen receptor activity of ENO1, and prevents cell dissociation from extracellular matrix.

Example 15

Biacore Analysis

Biacore analysis using a soluble ENO1 protein to bind antibodies immobilized on CM5 chips was performed for EN10 mAb to estimate their affinity for soluble antigen.

Figure 15A:
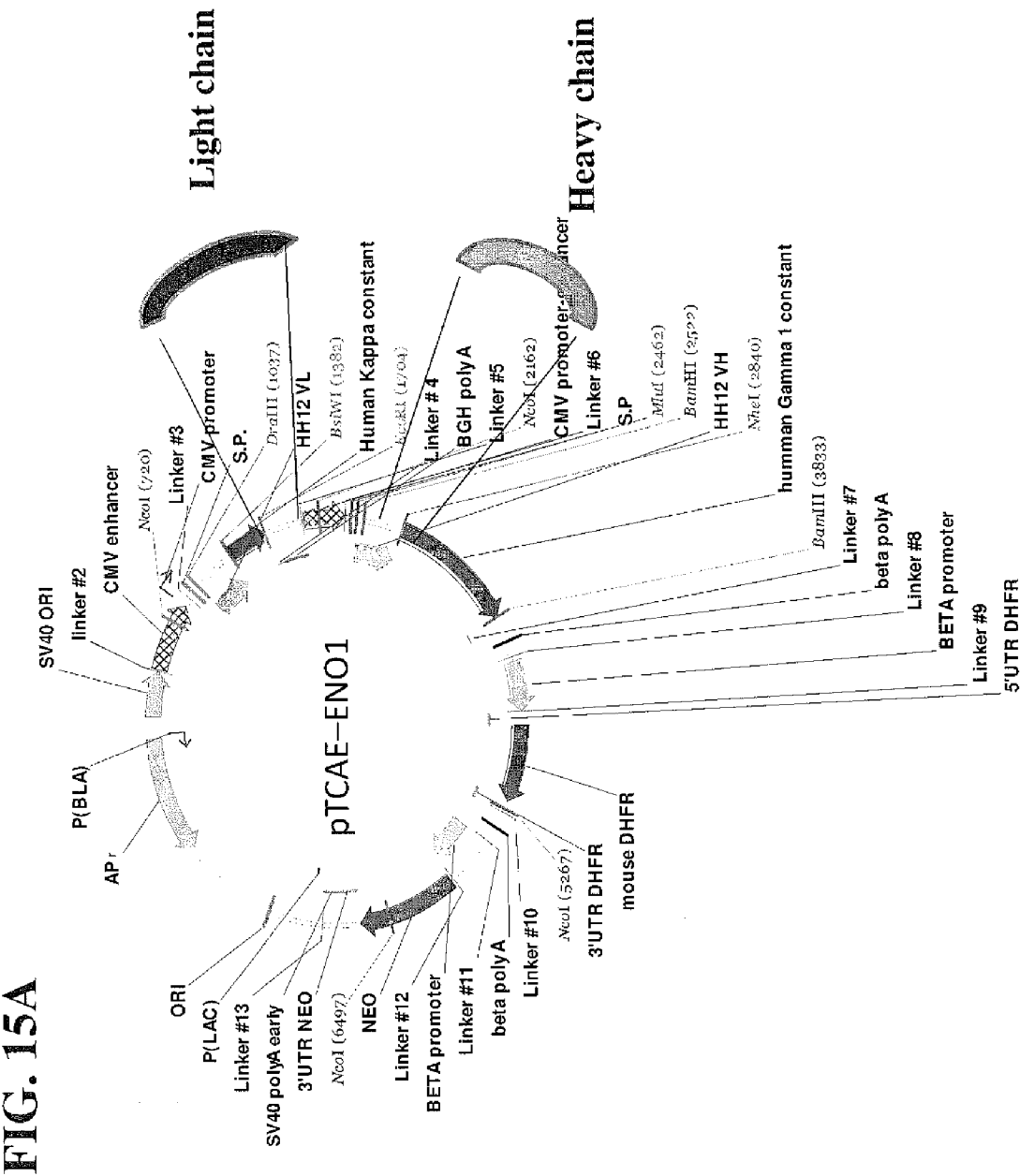
FIG. 15A shows an expression vector for the generation of mouse-human chimera of EN10 mAb. The detailed procedures for the purification of the EN10 mAb chimera antibody are described in Example 15.

The mouse variable region and human Fc chimera antibody expression vector pTCAE8-ENO1, as shown in FIG. 15A, was introduced into host cells to prepare recombinant antibody-expressing cells. As the host cells for expression, the FreeStyle293 cells (manufactured by Invitrogen) were used.

The vector was introduced into the host cells by lipofectamine 2000 in accordance with the attached instruction manual (manufactured by Invitrogen.) About 2.5 microgram of the antibody expression vector was linearized by restriction enzymes, the gene was introduced into $4 \times 10^6$ cells, and cells were inoculated to a 6-well culture plate. The agent corresponding to a selection marker of the expression vector was added, and cells were continuously cultured to form a stable pool.

A culture supernatant containing human IgG antibody was prepared by the method described below. The antibody-producing cells was acclimated in a Free Style™ 293 Expression Medium (GIBCO). The cells were cultured in a tissue culture flask, and the culture supernatant was collected when the viable rate of the cells was 90%. The collected supernatant was filtered through 10 micrometer and 0.2 micrometer filters (manufactured by Millpore) to remove contaminants. The culture supernatant containing the antibody was affinity-purified using Protein A (manufactured by Millipore), PBS as an absorption buffer, and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 MW cut, manufactured by Spectrum Laboratories) and filter-sterilized through a membrane filter (manufactured by Millpore) having a pore size of 0.22 micrometer to yield the purified antibody. The concentration of the purified antibody was determined by measuring the absorbance at 280 nm and converting the measured value based on 1.45 optimal density equaling 1 mg/ml.

For binding kinetics, surface plasmon resonance (SPR) measurement with a BIAcore 2000 (BIAcore, Inc., Piscataway, N.J.) was used as previously described (Karlsson & Falt, (1997) J. Immunol Methods 200:121-133). Carboxymethylated dextran biosensor chips (CM5, BIAcore Inc.) were activated with N-ethyl-N'-(3-dimethylaminopropyl)-carbodiimide hydrochloride (EDC) and N-hydroxysuccinimide (NHS) according to the supplier's instructions. Chimera EN10 mAb was diluted with 10 mM sodium acetate, pH 4.8, into 5 microgram/ml before injection at a flow rate of 20 micro L/minute to achieve approximately 100 response units (RU) of coupled protein followed by the injection of 1M ethanolamine to block unreacted groups. For kinetics measurements, two-fold serial dilutions of ENO1 (0.3125 nM to 40 nM) were injected in HBS-P Biacore running buffer provided by the manufacturer (BIAcore, Inc., Piscataway, N.J.) at 25 degree C. at a flow rate of 25 microL/min, and binding responses on the EN10 mAb were corrected by subtraction of responses on a blank flow cell. Association rates (kon or ka) and dissociation rates (koff or kd) were calculated using a simple one-to-one Langmuir binding model with separate fittings of kon and koff was used. (BIAcore™ Evaluation Software version 3.2).

TABLE 3

EN10 mAb

| ka | kd | $K_d$ | Rmax (RU) | Chi² (RU²) |
|---|---|---|---|---|
| 3.577E+5 | 8.271E-5 | 2.313E-10 | 176.8 | 0.668 |
| 3.575E+5 | 8.250E-5 | 2.308E-10 | 123.1 | 1.10 |
| 3.58 ± 0.01E+5 | 8.26 ± 0.01E-5 | 2.311 ± 0.003E-10 | 150 ± 38 | 0.88 ± 0.31 |

Figure 15B:
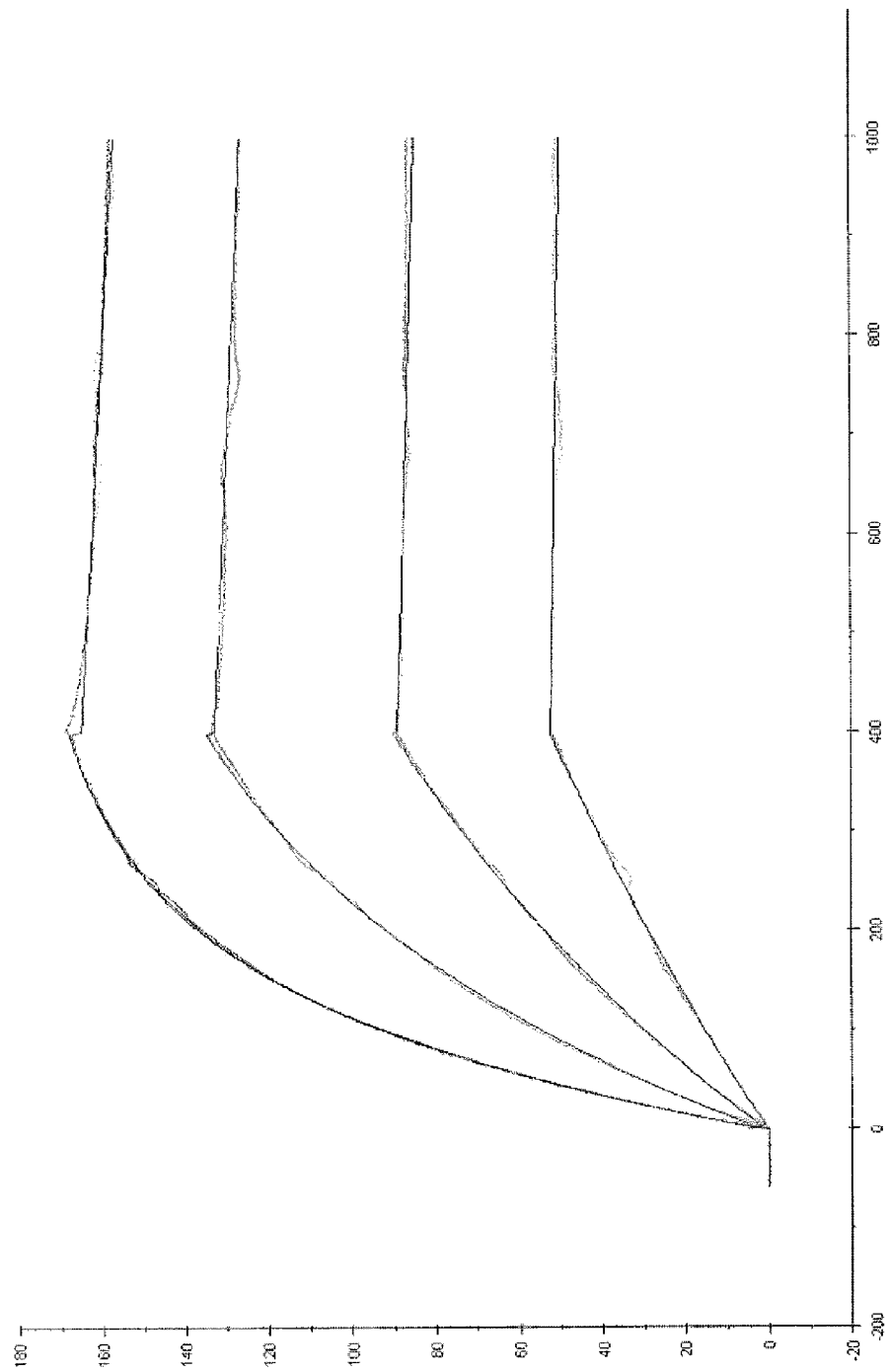
FIG. 15B depicts results from using the chimera antibody to determine binding affinity and kinetic constants of EN10 mAb. Detailed procedures of chimera antibody expression, purification and $K_d$ analysis were performed as described in Example 15.

The results are shown in the FIG. 15B and Table 3. The kon and koff of EN10 mAb binding with ENO1 are $3.57 \times 10^5$ and $8.271 \times 10^{-5}$, respectively, and $K_d$ is $2.311 \pm 0.003 \times 10^{-10}$ mol/L. The $K_d$ analyzed by SPR is very close to that of binding ELISA in the Example 2.

Example 16

Inhibitory Effect of the EN10 Antibody on Tumor Growth in the Presence of Complement The EN10 mAb has a good affinity with $K_d$ about $2.311 \pm 0.003 \times 10^{-10}$ mol/L and a potential for the further development. To evaluate the therapeutic effects of EN10 mAb, a CL1-5 mouse xenograft model was performed. CL1-5F4 lung adenocarcinoma cells ($1 \times 10^6$ cells/mouse; 5 mice/group) were subcutaneously inoculated at Day 0. The therapeutic procedure was performed 14 days after the tumor inoculation by administrating 10 mpk (mg/Kg) of an isotype control (CTL), EN10 mAb, or Erbitux™ antibody twice per week. The rabbit baby serum was given 2 h post-injection. The tumor volume and bodyweight of each mouse was measured weekly. Data are represented as mean±SD for individual groups.

Figure 16:
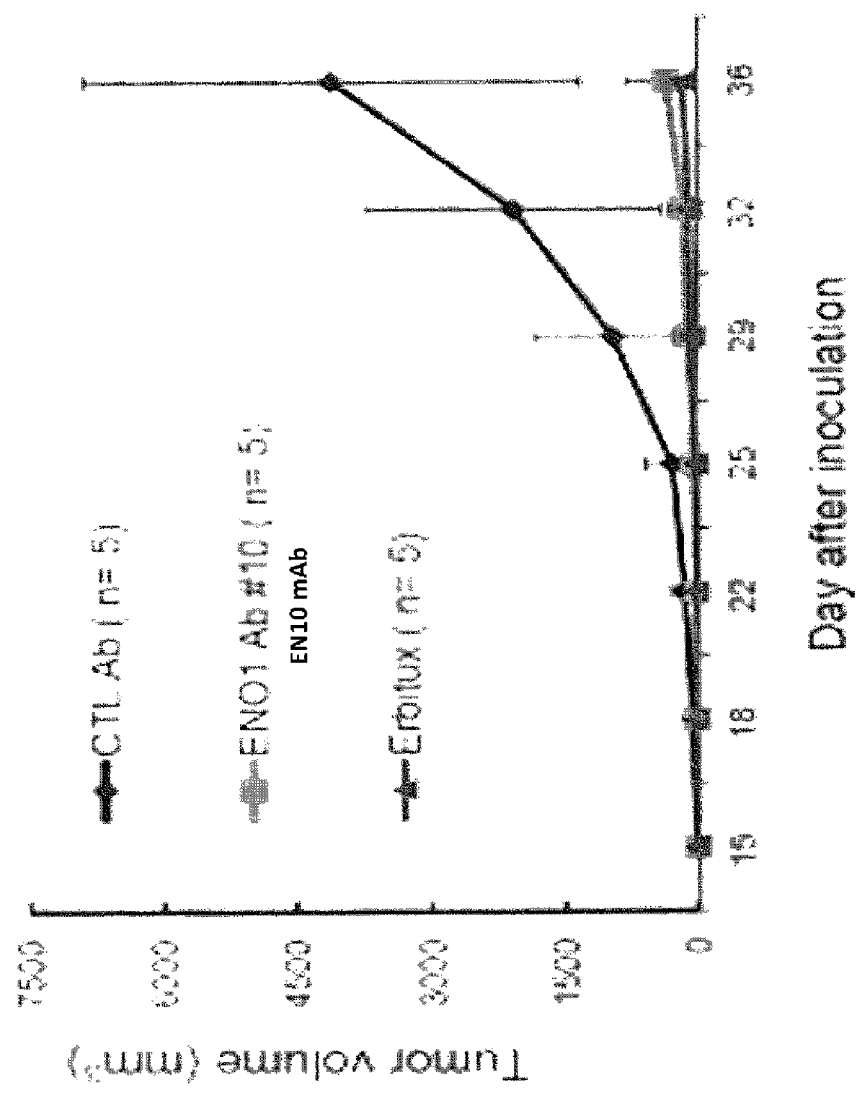
FIG. 16 shows inhibitory effects of EN10 mAb on the lung tumor growth in the presence of complement. The administration of EN10 mAb and the retardation of tumor growth by antibody treatment were performed as described in Example 16. The data show that the administration of EN10 mAb with complement twice per week has an efficacy similar to that treated with a same dose of commercial drug Erbitux™ in the CL1-5 xenograft mouse model.

The results are shown in FIG. 16. After 14 days the tumor sizes of mice bearing CL1-5 are about 30 to 100 mm³, and there are no significant tumor size differences among the control group, EN10 mAb, and Erbitux treatment groups after day 25. After day 29, the tumor of mice in the control group starts to grow exponentially, and there are no significant tumor growths in the Eribitux™ and EN10 mAb treatment mice. After day 36, the average tumor size of the control group mice is 4330±990 mm³ (N=5), and for mice treated with 10 mpk of EN10 mAb and Erbitux, the average tumor sizes are 358.6±240 mm³ (N=5) and 219±98 mm³ (N=5), respectively. The average tumor sizes of both EN10 mAb and Erbitux™ treatment groups are significantly smaller, as compared to that of the control group with a P value of 0.004 and 0.003, respectively. There are no significant tumor size difference tween EN10 mAb and Erbitux™ treatment groups (P=0.41). This result indicates that EN10 mAb and Erbitux have the tumor growth inhibition activity on CL1-5 cells when combined with complement C3 in the mouse xenograft model and EN10 mAb has a good efficacy as a reagent for cancer therapy.

Example 17

Blockade of Tumor Spread of Pancreatic Cancers in Spleen-Liver Metastatic Colony Formation Assay Results from Examples 2 and 3 suggest that administration of ENO1 antibody can attenuate the invasion and metastasis of cancer cells and results from Example 16 indicates that ENO1 mAb has efficacy in inhibiting the tumor growth when combined with complement. To evaluate the anti-metastatic activity of EN10 mAb on cancer cells in vivo, a spleen-liver metastatic assay were performed. PDAC1 pancreatic adenocarcinoma cells ($1 \times 10^6$/mouse; 5 mice/group) were injected into spleen. Then, 10 mpk of EN10 mAb and IgG control mice were administrated into each group by IP, respectively. The mice were scarified 6 weeks after tumor inoculation. The number of tumor nodules in livers and the weight of organs, including lungs, spleens, livers, pancreas, and kidneys, of each mouse were counted and measured, respectively. Data are represented as mean±SD for individual groups.

Figure 17A:
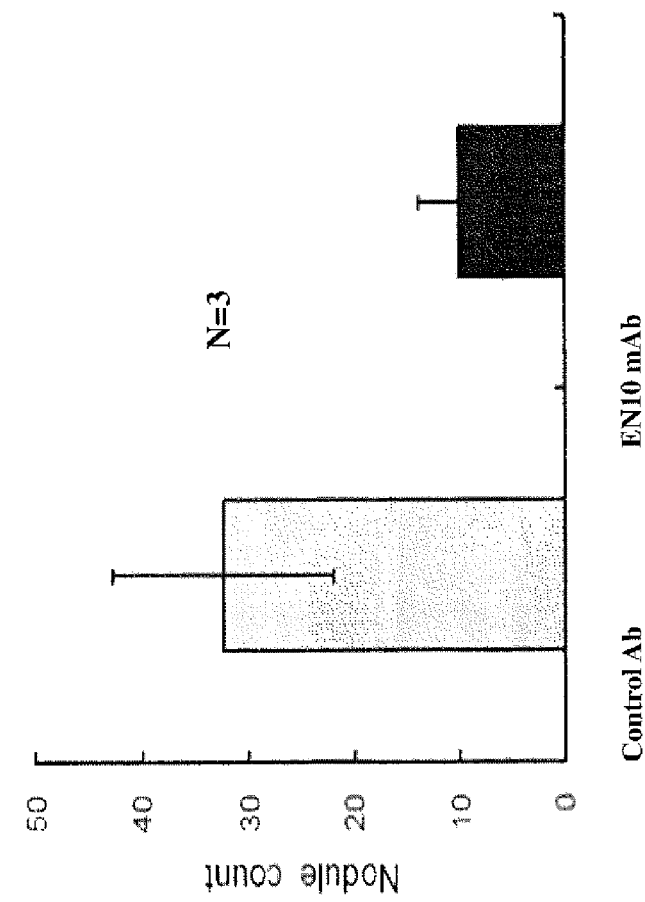
FIGS. 17A, 17B, and 17C show results from blockade of tumor spread of pancreatic cancers in spleen-liver metastatic colony formation assay by EN10 mAb. The administration of EN10 in mAb and the inhibition of metastatic tumor growth by antibody treatment were performed as described in Example 17. The study results indicate that the administration of 10 mpk (mg/kg) EN10 mAb twice per week decreases the metastatic tumor nodule numbers, tumor volumes, and tumor weights of mice compared to those of the same dose of control IgG in the spleen-liver metastatic mouse model.
Figure 17B:
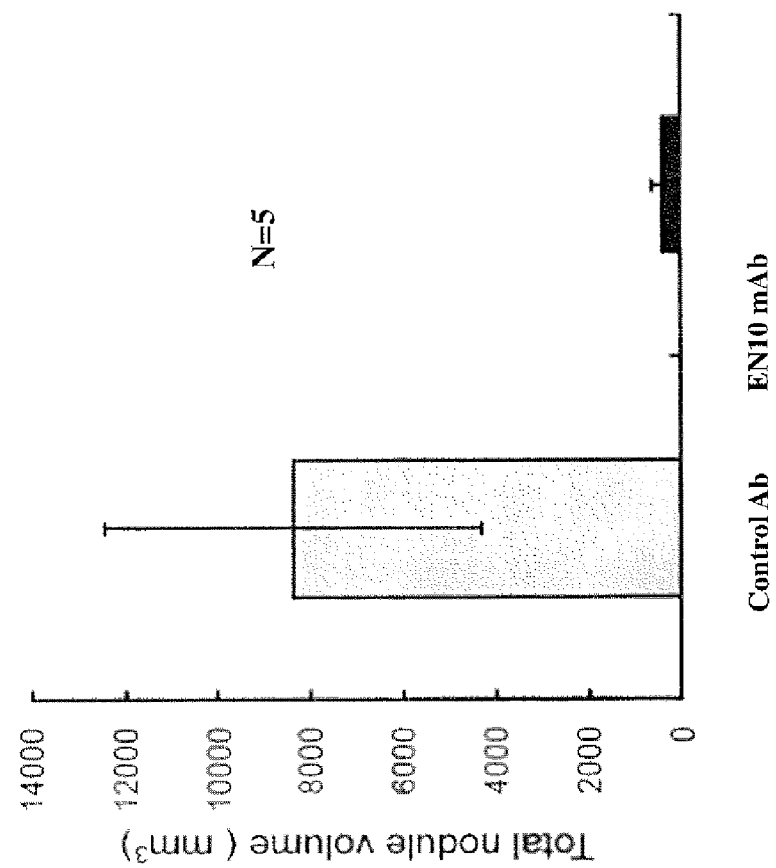
Figure 17C:
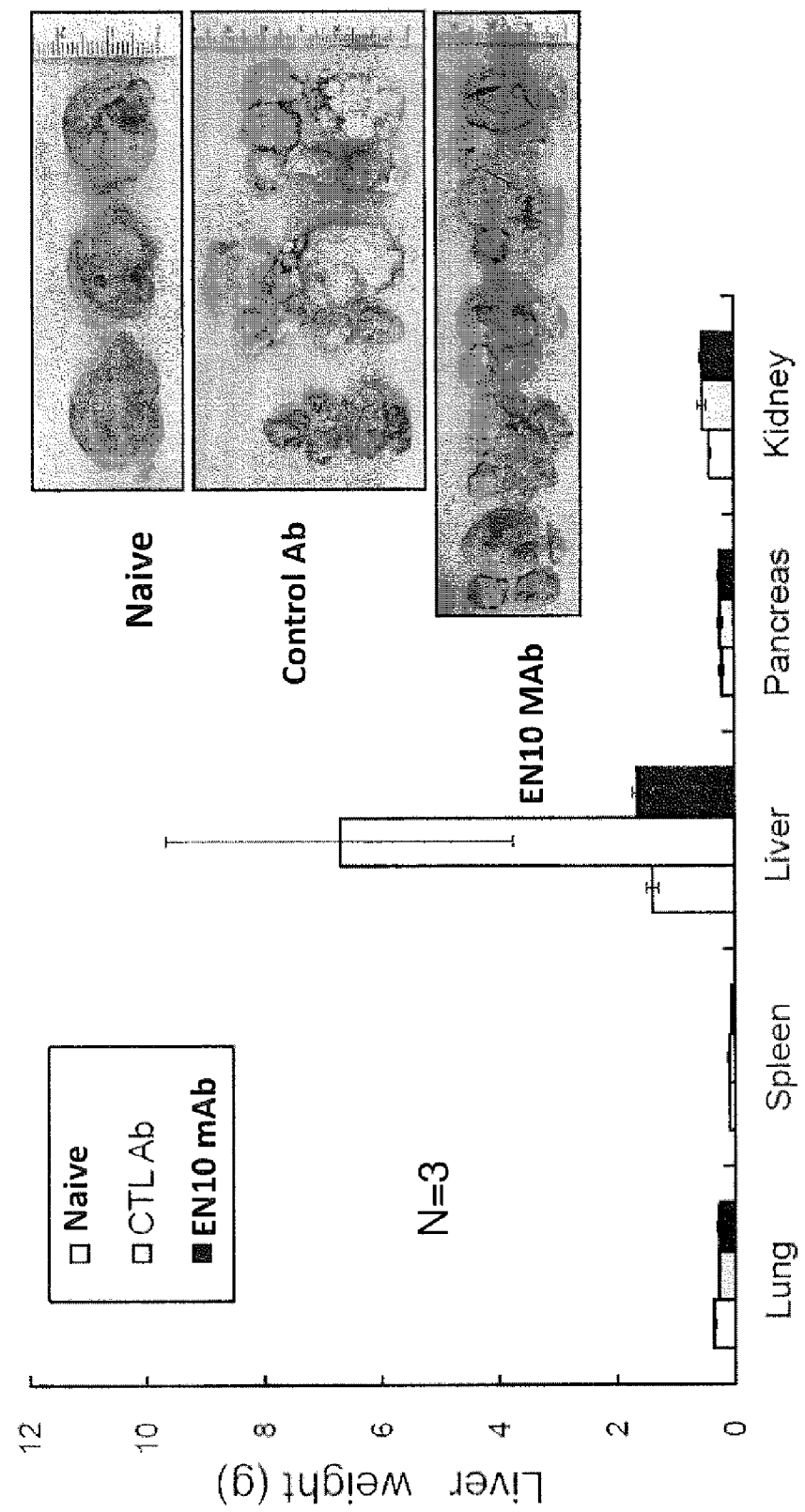

Results are shown in FIGS. 17A, 17B, and 17C. When liver tumor nodules and volumes are compared, the average tumor nodules and volumes of control IgG treated group are 34±10 (N=3) and 8500±3500 (N=5), respectively. However, as the same background mice were treated with 10 mpk of EN10 mAb, the average tumor nodules and volumes of treated mice are 10±4 (N=3) and 500±120 (N=5), respectively. There are significant tumor nodule number and volume differences between 10 mpk ENO1 and the control IgG treated groups (P<0.05) (FIGS. 17A and 17B). When average weights of organs were compared between the 10 mpk ENO1 and the control IgG treatment groups, there are no significant organ weight differences, including lungs, spleens, pancreases, and kidneys. However, mice treated with 10 mpk IgG has an average liver weight about 7.2±3 g (N=5), which is statistic different, as compared to that of mice treated with 10 mpk EN10 mAb (1.6±0.2 g (N=5), P<0.05). These results suggest that administration of EN10 mAb inhibits the metastasis of PDAC1 cells from primary tumor site to the liver.

In sum, EN10 mAb uses its ENO1 plasminogen receptor antagonist activity to inhibit the plasminogen activation, thereby inducing down regulation of protease activity on the cell surface, which in turn results in the inhibition of dissociation of cancer cells from extracellular matrix. As a result, antibodies against ENO1 can inhibit the invasion capability of cancer cells. These data support that ENO1 antibodies (e.g., EN10 mAb) have favorable affinity, efficacy and potential as a therapeutic antibody for the treatment of cancers.

In addition to inhibiting cancer dissociation from extracellular matrix and, therefore, inhibiting cancer invasion, an antibody of the invention may also be used to diagnose a cancerous condition. As noted above and shown in FIG. 1A and FIG. 1B, cancer cells express ENO1 on cell surfaces, while normal cells do not. Therefore, one can detect antibody binding to cell surface ENO1 as an indication of cancerous conditions.

For example, in accordance with embodiments of the invention, a test sample may be reacted with an anti-ENO1 antibody (e.g., EN10 mAb) and the binding of the antibody to the sample may be determined, such as with ELISA, fluorescence cell sorting, fluorescence microscope, or any suitable method known in the art. If the binding is detected or is above a threshold value (e.g., a reference value for a normal sample), then one may conclude that the sample contains cancer cells.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An anti-human alpha-enolase-1 (ENO1) antibody, or an scFv or Fab fragment thereof, comprising the following complimentarity determining sequences: HCDR1 (GYTFTSCVMN; SEQ ID NO:3), HCDR2 (YINPYNDGTKYNEKFKG; SEQ ID NO:4), HCDR3 (EGFYYGNFDN; SEQ ID NO:5), LCDR1 (RASENIYSYLT; SEQ ID NO:6), LCDR2 (NAKTLPE; SEQ ID NO:7), and LCDR3 (QHHYGTPYT; SEQ ID NO:8).

2. The anti-human alpha-enolase-1 (ENO1) antibody, or the scFv or Fab fragment thereof, according to claim 1, comprising a heavy chain that comprises the sequences of HCDR1 (GYTFTSCVMN; SEQ ID NO:3), HCDR2 (YINPYNDGTKYNEKFKG; SEQ ID NO:4), and HCDR3 (EGFYYGNFDN; SEQ ID NO:5).

3. The anti-human alpha-enolase-1 (ENO1) antibody, or the scFv or Fab fragment thereof, according to claim 2, wherein the heavy chain comprises the sequence of SEQ ID NO:1.

4. The anti-human alpha-enolase-1 (ENO1) antibody, or the scFv or Fab fragment thereof, according to claim 1, comprising a light chain that comprises the sequences of LCDR1 (RASENIYSYLT; SEQ ID NO:6), LCDR2 (NAKTLPE; SEQ ID NO:7), and LCDR3 (QHHYGTPYT; SEQ ID NO:8).

5. The anti-human alpha-enolase-1 (ENO1) antibody, or the scFv or Fab fragment thereof, according to claim 4, wherein the light chain comprises the sequence of SEQ ID NO:2.

6. The anti-human alpha-enolase-1 (ENO1) antibody, or the scFv or Fab fragment thereof, according to claim 1, comprising a heavy chain that comprises the sequences of HCDR1 (GYTFTSCVMN; SEQ ID NO:3), HCDR2 (YINPYNDGTKYNEKFKG; SEQ ID NO:4), and HCDR3 (EGFYYGNFDN; SEQ ID NO:5) and a light chain that comprises the sequences of LCDR1 (RASENIYSYLT; SEQ ID NO:6), LCDR2 (NAKTLPE; SEQ ID NO:7), and LCDR3 (QHHYGTPYT; SEQ ID NO:8).

7. The anti-human alpha-enolase-1 (ENO1) antibody, or the scFv or Fab fragment thereof, according to claim 6, wherein the heavy chain comprises the sequence of SEQ ID NO:1 and the light chain comprises the sequence of SEQ ID NO:2.

8. The anti-human alpha-enolase-1 (ENO1) antibody, or the scFv or Fab fragment thereof, according to claim 1, wherein the antibody, or the scFv or Fab fragment thereof, can bind ENO1.

9. The anti-human alpha-enolase-1 (ENO1) antibody, or the scFv or Fab fragment thereof, according to claim 8, wherein the antibody, or the scFv or Fab fragment thereof, can inhibit plasminogen receptor activity of ENO1.

10. The anti-human alpha-enolase-1 (ENO1) antibody, or the scFv or Fab fragment thereof, according to claim 1, wherein the antibody is a monoclonal antibody.

11. An anti-human alpha-enolase-1 (ENO1) antibody, or an scFv or Fab fragment thereof, wherein the antibody, or the scFv or Fab fragment thereof, can bind to an epitope consisting of the sequence of FDQDDWGA WQKFTA (SEQ ID NO:9) or KRIAKAVNEKS (SEQ ID NO:10) with a dissociation constant ($K_d$) of 10 nM or lower.

12. The anti-human alpha-enolase-1 (ENO1) antibody, or the scFv or Fab fragment thereof, according to claim 11, wherein the epitope comprises the sequence of FDQDDWGAWQKFTASAGIQVVGDDLTVTNPKRIAKAVNEKS (SEQ ID NO:49).

13. The anti-human alpha-enolase-1 (ENO1) antibody, or the scFv or Fab fragment thereof, according to claim 11, wherein the antibody, or the scFv or Fab fragment thereof, can inhibit plasminogen receptor activity of ENO1.

14. The anti-human alpha-enolase-1 (ENO1) antibody, or the scFv or Fab fragment thereof, according to claim 11, wherein the antibody is a monoclonal antibody.

15. A pharmaceutical composition for treating lung, breast, pancreas, liver, colorectal, or prostate cancer, comprising the anti-human alpha-enolase-1 (ENO1) antibody, or the scFv or Fab fragment thereof, according to claim 1.

16. A pharmaceutical composition for treating lung, breast, pancreas, liver, colorectal, or prostate cancer, comprising the anti-human alpha-enolase-1 (ENO1) antibody, or the scFv or Fab fragment thereof, according to claim 11.

17. A method for diagnosis of cancer, comprising:
reacting a sample from a test subject with the anti-human alpha-enolase-1 (ENO1) antibody, or the scFv or Fab fragment thereof, of claim 1 to determine an extent of binding; wherein the extent of binding greater than a reference value indicates a cancerous condition.

18. A method for diagnosis of cancer, comprising: reacting a sample from a test subject with the anti-human alpha-enolase-1 (ENO1) antibody, or the scFv or Fab fragment thereof, of claim 11 to determine an extent of binding; wherein the extent of binding greater than a reference value indicates a cancerous condition.

19. A method for inhibiting cancer invasion, comprising:
administering to a subject in need thereof the anti-human alpha-enolase-1 (ENO1) antibody, or the scFv or Fab fragment thereof, of claim 1.

20. A method for inhibiting cancer invasion, comprising:
administering to a subject in need thereof the anti-human alpha-enolase-1 (ENO1) antibody, or the scFv or Fab fragment thereof, of claim 11.

* * * * *

SEQUENCE LISTING

<160> NUMBER OF SEQ ID NOS: 49

<210> SEQ ID NO 1
<211> LENGTH: 119
<212> TYPE: PRT
<213> ORGANISM: Mus musculus

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Cys
            20                  25                  30

Val Met Asn Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Phe Tyr Tyr Gly Asn Phe Asp Asn Trp Gly Gln Gly
            100                 105                 110

Thr Thr Leu Thr Val Ser Ser
            115

<210> SEQ ID NO 2
<211> LENGTH: 108
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Tyr
                85                  90                  95

Thr Phe Gly Gly Gly Thr Lys Leu Glu Ile Thr Arg
            100                 105

<210> SEQ ID NO 3
<211> LENGTH: 10
<212> TYPE: PRT
<213> ORGANISM: Mus musculus

<400> SEQUENCE: 3

Gly Tyr Thr Phe Thr Ser Cys Val Met Asn
1               5                   10

<210> SEQ ID NO 4
<211> LENGTH: 17
<212> TYPE: PRT
<213> ORGANISM: Mus musculus

```
<400> SEQUENCE: 4

Tyr Ile Asn Pro Tyr Asn Asp Gly Thr Lys Tyr Asn Glu Lys Phe Lys
1               5                   10                  15

Gly

<210> SEQ ID NO 5
<211> LENGTH: 9
<212> TYPE: PRT
<213> ORGANISM: Mus musculus

<400> SEQUENCE: 5

Gly Phe Tyr Tyr Gly Asn Phe Asp Asn
1               5

<210> SEQ ID NO 6
<211> LENGTH: 11
<212> TYPE: PRT
<213> ORGANISM: Mus musculus

<400> SEQUENCE: 6

Arg Ala Ser Glu Asn Ile Tyr Ser Tyr Leu Thr
1               5                   10

<210> SEQ ID NO 7
<211> LENGTH: 7
<212> TYPE: PRT
<213> ORGANISM: Mus musculus

<400> SEQUENCE: 7

Asn Ala Lys Thr Leu Pro Glu
1               5

<210> SEQ ID NO 8
<211> LENGTH: 9
<212> TYPE: PRT
<213> ORGANISM: Mus musculus

<400> SEQUENCE: 8

Gln His His Tyr Gly Thr Pro Tyr Thr
1               5

<210> SEQ ID NO 9
<211> LENGTH: 14
<212> TYPE: PRT
<213> ORGANISM: Homo sapiens

<400> SEQUENCE: 9

Phe Asp Gln Asp Asp Trp Gly Ala Trp Gln Lys Phe Thr Ala
1               5                   10

<210> SEQ ID NO 10
<211> LENGTH: 11
<212> TYPE: PRT
<213> ORGANISM: Homo sapiens

<400> SEQUENCE: 10

Lys Arg Ile Ala Lys Ala Val Asn Glu Lys Ser
1               5                   10

<210> SEQ ID NO 11
<211> LENGTH: 18
<212> TYPE: DNA
<213> ORGANISM: artificial
```

<220> FEATURE:
<223> OTHER INFORMATION: synthetic

<400> SEQUENCE: 11
gtaaacaacg acggcgag						18

<210> SEQ ID NO 12
<211> LENGTH: 17
<212> TYPE: DNA
<213> ORGANISM: artificial
<220> FEATURE:
<223> OTHER INFORMATION: synthetic

<400> SEQUENCE: 12
caggaaacag ctatgac						17

<210> SEQ ID NO 13
<211> LENGTH: 30
<212> TYPE: DNA
<213> ORGANISM: artificial
<220> FEATURE:
<223> OTHER INFORMATION: synthetic

<400> SEQUENCE: 13
ggatccgcag caaacttcag ggaagccatg					30

<210> SEQ ID NO 14
<211> LENGTH: 30
<212> TYPE: DNA
<213> ORGANISM: artificial
<220> FEATURE:
<223> OTHER INFORMATION: synthetic

<400> SEQUENCE: 14
ggatcctcga agatcccttt gaccaggatg					30

<210> SEQ ID NO 15
<211> LENGTH: 24
<212> TYPE: DNA
<213> ORGANISM: artificial
<220> FEATURE:
<223> OTHER INFORMATION: synthetic

<400> SEQUENCE: 15
tcaggctgaa aatctctcat ccgc					24

<210> SEQ ID NO 16
<211> LENGTH: 29
<212> TYPE: DNA
<213> ORGANISM: artificial
<220> FEATURE:
<223> OTHER INFORMATION: synthetic

<400> SEQUENCE: 16
ggatcctatc tattctcaag atccatgcc					29

<210> SEQ ID NO 17
<211> LENGTH: 33
<212> TYPE: DNA
<213> ORGANISM: artificial
<220> FEATURE:
<223> OTHER INFORMATION: synthetic

<400> SEQUENCE: 17
ctcgaggtca tggtgtctca tcgttcgctc gag				33

<210> SEQ ID NO 18
<211> LENGTH: 32
<212> TYPE: DNA
<213> ORGANISM: artificial
<220> FEATURE:
<223> OTHER INFORMATION: synthetic

<400> SEQUENCE: 18
ctcgagaggg atcttcgata gacaccactg gg                     32

<210> SEQ ID NO 19
<211> LENGTH: 30
<212> TYPE: DNA
<213> ORGANISM: artificial
<220> FEATURE:
<223> OTHER INFORMATION: synthetic

<400> SEQUENCE: 19
ctcgagctac ctggattcct gcactggctg                        30

<210> SEQ ID NO 20
<211> LENGTH: 32
<212> TYPE: DNA
<213> ORGANISM: artificial
<220> FEATURE:
<223> OTHER INFORMATION: synthetic

<400> SEQUENCE: 20
ctcgagactt ctcgttcacg gccttggcga tc                     32

<210> SEQ ID NO 21
<211> LENGTH: 33
<212> TYPE: DNA
<213> ORGANISM: artificial
<220> FEATURE:
<223> OTHER INFORMATION: synthetic

<400> SEQUENCE: 21
ctcgagactt ctcgttcacg gccttggcga tcc                    33

<210> SEQ ID NO 22
<211> LENGTH: 32
<212> TYPE: DNA
<213> ORGANISM: artificial
<220> FEATURE:
<223> OTHER INFORMATION: synthetic

<400> SEQUENCE: 22
ctcgagcagt ctcccccgaa cgatgagaca cc                     32

<210> SEQ ID NO 23
<211> LENGTH: 32
<212> TYPE: DNA
<213> ORGANISM: artificial
<220> FEATURE:
<223> OTHER INFORMATION: synthetic

<400> SEQUENCE: 23
ctcgagcacc agtcttgatc tgcccagtgc ac                     32

<210> SEQ ID NO 24
<211> LENGTH: 36
<212> TYPE: DNA
<213> ORGANISM: artificial
<220> FEATURE:
<223> OTHER INFORMATION: synthetic

<400> SEQUENCE: 24 gatcccttg accaggatgc ctggggagct tggcag        36

<210> SEQ ID NO 25
<211> LENGTH: 36
<212> TYPE: DNA
<213> ORGANISM: artificial
<220> FEATURE:
<223> OTHER INFORMATION: synthetic

<400> SEQUENCE: 25
ctgccaagct ccccaggcat cctggtcaaa gggatc        36

<210> SEQ ID NO 26
<211> LENGTH: 36
<212> TYPE: DNA
<213> ORGANISM: artificial
<220> FEATURE:
<223> OTHER INFORMATION: synthetic

<400> SEQUENCE: 26
ccctttgacc aggatgacgc gggagcttgg cagaag        36

<210> SEQ ID NO 27
<211> LENGTH: 36
<212> TYPE: DNA
<213> ORGANISM: artificial
<220> FEATURE:
<223> OTHER INFORMATION: synthetic

<400> SEQUENCE: 27
cttctgccaa gctcccgcgt catcctggtc aaaggg        36

<210> SEQ ID NO 28
<211> LENGTH: 37
<212> TYPE: DNA
<213> ORGANISM: artificial
<220> FEATURE:
<223> OTHER INFORMATION: synthetic

<400> SEQUENCE: 28
ctttgaccag gatgactggg cagcttggca gaagttc        37

<210> SEQ ID NO 29
<211> LENGTH: 37
<212> TYPE: DNA
<213> ORGANISM: artificial
<220> FEATURE:
<223> OTHER INFORMATION: synthetic

<400> SEQUENCE: 29
gaacttctgc caagctgccc agtcatcctg gtcaaag        37

<210> SEQ ID NO 30
<211> LENGTH: 36
<212> TYPE: DNA
<213> ORGANISM: artificial
<220> FEATURE:
<223> OTHER INFORMATION: synthetic

<400> SEQUENCE: 30
gactggggag cttgggcgaa gttcacagcc agtgca        36

<210> SEQ ID NO 31

```
<211> LENGTH: 36
<212> TYPE: DNA
<213> ORGANISM: artificial
<220> FEATURE:
<223> OTHER INFORMATION: synthetic

<400> SEQUENCE: 31
tgcactggct gtgaacttcg cccaagctcc ccagtc                              36

<210> SEQ ID NO 32
<211> LENGTH: 34
<212> TYPE: DNA
<213> ORGANISM: artificial
<220> FEATURE:
<223> OTHER INFORMATION: synthetic

<400> SEQUENCE: 32
ggggagcttg gcaggcgttc acagccagtg cagg                               34

<210> SEQ ID NO 33
<211> LENGTH: 34
<212> TYPE: DNA
<213> ORGANISM: artificial
<220> FEATURE:
<223> OTHER INFORMATION: synthetic

<400> SEQUENCE: 33
cctgcactgg ctgtgaacgc ctgccaagct cccc                               34

<210> SEQ ID NO 34
<211> LENGTH: 36
<212> TYPE: DNA
<213> ORGANISM: artificial
<220> FEATURE:
<223> OTHER INFORMATION: synthetic

<400> SEQUENCE: 34
ggcagaagtt cacaggcagt gcaggaatcc aggtag                             36

<210> SEQ ID NO 35
<211> LENGTH: 36
<212> TYPE: DNA
<213> ORGANISM: artificial
<220> FEATURE:
<223> OTHER INFORMATION: synthetic

<400> SEQUENCE: 35
ctacctggat tcctgcactg cctgtgaact tctgcc                             36

<210> SEQ ID NO 36
<211> LENGTH: 35
<212> TYPE: DNA
<213> ORGANISM: artificial
<220> FEATURE:
<223> OTHER INFORMATION: synthetic

<400> SEQUENCE: 36
tcacagtgac caacccagcg aggatcgcca aggcc                              35

<210> SEQ ID NO 37
<211> LENGTH: 35
<212> TYPE: DNA
<213> ORGANISM: artificial
<220> FEATURE:
<223> OTHER INFORMATION: synthetic

<400> SEQUENCE: 37
```
gccttggcga tcctcgctgg gttggtcact gtgag                         35

<210> SEQ ID NO 38
<211> LENGTH: 37
<212> TYPE: DNA
<213> ORGANISM: artificial
<220> FEATURE:
<223> OTHER INFORMATION: synthetic

<400> SEQUENCE: 38
caacccaaag aggatcgccg cggccgtgaa cgagaag                       37

<210> SEQ ID NO 39
<211> LENGTH: 37
<212> TYPE: DNA
<213> ORGANISM: artificial
<220> FEATURE:
<223> OTHER INFORMATION: synthetic

<400> SEQUENCE: 39
cttctcgttc acggccgcgg cgatcctctt tgggttg                       37

<210> SEQ ID NO 40
<211> LENGTH: 37
<212> TYPE: DNA
<213> ORGANISM: artificial
<220> FEATURE:
<223> OTHER INFORMATION: synthetic

<400> SEQUENCE: 40
gaggatcgcc aaggccgtgg ccgagaagtc ctgcaac                       37

<210> SEQ ID NO 41
<211> LENGTH: 37
<212> TYPE: DNA
<213> ORGANISM: artificial
<220> FEATURE:
<223> OTHER INFORMATION: synthetic

<400> SEQUENCE: 41
gttgcaggac ttctcggcca cggccttggc gatcctc                       37

<210> SEQ ID NO 42
<211> LENGTH: 36
<212> TYPE: DNA
<213> ORGANISM: artificial
<220> FEATURE:
<223> OTHER INFORMATION: synthetic

<400> SEQUENCE: 42
gatcgccaag gccgtgaacg cgaagtcctg caactg                        36

<210> SEQ ID NO 43
<211> LENGTH: 37
<212> TYPE: DNA
<213> ORGANISM: artificial
<220> FEATURE:
<223> OTHER INFORMATION: synthetic

<400> SEQUENCE: 43
gcagttgcag gacttcgcgt tcacggcctt ggcgatc                       37

<210> SEQ ID NO 44
<211> LENGTH: 36
<212> TYPE: DNA
<213> ORGANISM: artificial
<220> FEATURE:
<223> OTHER INFORMATION: synthetic

<400> SEQUENCE: 44
gccaaggccg tgaacgaggc gtcctgcaac tgcctc                         36

<210> SEQ ID NO 45
<211> LENGTH: 36
<212> TYPE: DNA
<213> ORGANISM: artificial
<220> FEATURE:
<223> OTHER INFORMATION: synthetic

<400> SEQUENCE: 45
gaggcagttg caggacgcct cgttcacggc cttggc                         36

<210> SEQ ID NO 46
<211> LENGTH: 37
<212> TYPE: DNA
<213> ORGANISM: artificial
<220> FEATURE:
<223> OTHER INFORMATION: synthetic

<400> SEQUENCE: 46
caaggccgtg aacgcggcgt cctgcaactg cctcctg                        37

<210> SEQ ID NO 47
<211> LENGTH: 37
<212> TYPE: DNA
<213> ORGANISM: artificial
<220> FEATURE:
<223> OTHER INFORMATION: synthetic

<400> SEQUENCE: 47
caggaggcag ttgcaggacg ccgcgttcac ggccttg                        37

<210> SEQ ID NO 48
<211> LENGTH: 24
<212> TYPE: DNA
<213> ORGANISM: artificial
<220> FEATURE:
<223> OTHER INFORMATION: synthetic

<400> SEQUENCE: 48
gcaaggggca ccagtcttga tctg                                      24

<210> SEQ ID NO 49
<211> LENGTH: 41
<212> TYPE: PRT
<213> ORGANISM: Homo sapiens

<400> SEQUENCE: 49

Phe Asp Gln Asp Asp Trp Gly Ala Trp Gln Lys Phe Thr Ala Ser Ala
1               5                   10                  15

Gly Ile Gln Val Val Gly Asp Asp Leu Thr Val Thr Asn Pro Lys Arg
            20                  25                  30

Ile Ala Lys Ala Val Asn Glu Lys Ser
        35                  40